US010184211B2

(12) United States Patent
Kim et al.

(10) Patent No.: US 10,184,211 B2
(45) Date of Patent: Jan. 22, 2019

(54) SURFACE MODIFIED POLYMERIC NANOFIBER SUBSTRATES BY PLASMA TREATMENT AND FABRICATION PROCESS FOR THE SAME

(71) Applicant: RESEARCH & BUSINESS FOUNDATION SUNGKYUNKWAN UNIVERSITY, Suwon-si (KR)

(72) Inventors: Geunhyung Kim, Seongnam-si (KR); HoJun Jeon, Suwon-si (KR); Gyuhyun Jin, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 901 days.

(21) Appl. No.: 14/553,433

(22) Filed: Nov. 25, 2014

(65) Prior Publication Data

US 2015/0225892 A1    Aug. 13, 2015

(30) Foreign Application Priority Data

Feb. 10, 2014    (KR) .......................... 10-2014-0014770

(51) Int. Cl.
| | |
|---|---|
| *D06M 10/02* | (2006.01) |
| *C12N 5/00* | (2006.01) |
| *A61L 27/18* | (2006.01) |
| *A61L 27/50* | (2006.01) |
| *A61L 27/58* | (2006.01) |

(Continued)

(52) U.S. Cl.
CPC .......... *D06M 10/025* (2013.01); *A61L 27/18* (2013.01); *A61L 27/50* (2013.01); *A61L 27/58* (2013.01); *C12N 5/0068* (2013.01); *D06M 23/16* (2013.01); *A61L 2400/12* (2013.01); *A61L 2400/18* (2013.01); *C12N 2533/40* (2013.01); *D06M 2101/32* (2013.01); *Y10T 428/24355* (2015.01)

(58) Field of Classification Search
CPC ................................................... D06M 10/025
See application file for complete search history.

(56) References Cited

FOREIGN PATENT DOCUMENTS

CN        102093586 A    *    6/2011

OTHER PUBLICATIONS

Martins et al. Surface Modification of Electrospun Polycaprolactone Nanofiber Meshes by Plasma Treatment to Enhance Biological Performance. Small 2009, 5, No. 10, 1195-1206 (Year: 2009).*

(Continued)

*Primary Examiner* — Cachet I Sellman
(74) *Attorney, Agent, or Firm* — NSIP Law

(57) ABSTRACT

A method of modifying a surface of a polymeric nanofiber, for example, a polymeric nanofiber mat, is provided. For surface modification of the polymeric nanofiber by plasma treatment, a method capable of forming a surface of the polymeric nanofiber on nano-scaled patterns using a remarkably simple method in which the polymeric nanofiber is subjected to plasma treatment in a state in which an AAO template is placed on the polymeric nanofiber is provided. Ultimately, the invention for obtaining a biomaterial for tissue regeneration applications by providing micro-environmental conditions, which are more desirable to initial attachment and growth of cells, to a surface of the polymeric nanofiber is disclosed.

7 Claims, 15 Drawing Sheets

An Electrospinning Process

(51) Int. Cl.
*D06M 23/16* (2006.01)
*D06M 101/32* (2006.01)

(56) References Cited

OTHER PUBLICATIONS

Sulka et al. Anodic Porous Alumina as a Template for Nanofabrication. Encyclopedia of Nanoscience and Nanotechnology Edited by H. S. Nalwa vol. 11: pp. 261-349 (Year: 2011).*
Nandakumar et al. Surface modification of electrospun fibre meshes by oxygen plasma for bone regeneration. Biofabrication 5 (2013) 015006 (14pp) (Year: 2013).*
Lei et al. Highly ordered nanostructures with tunable size, shape and properties: A new way to surface nano-patterning using ultra-thin alumina masks. Progress in Materials Science 52 (2007) 465-539 (Year: 2007).*
Ohl et al. Plasma-induced chemical micropatterning for cell culturing applications: a brief review. Surface and Coatings Technology 116-119 (1999) 820-830 (Year: 1999).*
Sardella et al. Plasma-Aided Micro- and Nanopatterning Processes for Biomedical Applications. Plasma Process. Polym. 2006, 3, 456-469 (Year: 2006).*
Jeon et al. Nanosized Surface Patterns on Electrospun Microfibers Fabricated Using a Modified Plasma Process for Enhancing Intial Cellular Activities. Plasma Processes and Polymers. Dec. 9, 2013 (Year: 2013).*
Nandakumar et al. Surface Modification of electrospun fibre meshes by oxygen plasma for bone regeneration. Biofabrication 5 pp. 1-14 (Year: 2013).*
Little et al. Surface modification of poly(e-caprolactone) using a dielectric barrier discharge in atmospheric pressure glow discharge mode. Acta Biomaterilia. vol. 5 pp. 2025-2032 (Year: 2009).*
Hashemi et al.Poly (e-caprolactone) nanofibrous ring surrounding a polyvinyl alcohol hydrogel for development of a biocompatible two part artificial cornea. International Journal of Nanomedicine. (Year: 2011).*
"SungKyunKwan University's professor Kim, Geunhyung research team develop nano pattern cell carrier for reproducing damaged human tissues." Dcinside.com, Dec. 15, 2013 (3 pages, in Korean, with partial English translation).
"Korean Scientist (Professor Kim, Geunhyung)" Etnews.com, Dec. 15, 2013 (3 pages, in Korean, with partial English translation).
"Professor Kim, Geunhyung succeed in nano pattern cell carrier for reproducing damaged human tissues." *Korean college journal*, Dec. 16, 2013 (2 pages, in Korean, with partial English translation).
"Professor Kim, Geunhyung's Research Team of Sungkyunkwan University, Papers Published on the Cover of Royal Society of Chemistry" *Popular opinion*, Dec. 12, 2013. (3 pages, in Korean, with partial English translation).
"Professor Kim Geunhyung's Research Team of Sungkyunkwan University, Papers Published on the Cover of Royal Society of Chemistry" *ASIATODAY*, Dec. 12, 2013 (3 pages, in Korean, with partial English translation).
"SungKyunKwan University Professor Kim Geunhyung's research team develop nano pattern cell carrier for reproducing damaged human tissues" *SKKU*, Dec. 12, 2013 (4 pages, in Korean, with partial English translation).
Jeon, HoJun, et al. "Preparation and characterization of an electrospun polycaprolactone (PCL) fibrous mat and multi-layered PCL scaffolds having a nanosized pattern-surface for tissue regeneration." Journal of Materials Chemistry B 2.2, 2014: (12 pages).
Jeon, Ho Jun, et al. "Nano-Sized Surface Patterns on Electrospun Microfibers Fabricated Using a Modified Plasma Process for Enhancing Initial Cellular Activities." Plasma Processes and Polymers 11.2, 2014: (15 pages).
Yan, Da, et al. "Plasma treatment of random and aligned electrospun pcl nanofibers." Journal of Medical and Biological Engineering 33.2 (2013): 171-178.
Eom, Seon-Mi, et al. "A Study of the Preparation and Application of Au/TiO2 Nanofiber from AAO Template" Journal of the Korean Electrochemical Society vol. 12, No. 1, 2009, 47-53.
Chen, Jyh-Ping, et al. "Surface modification of electrospun PLLA nanofibers by plasma treatment and cationized gelatin immobilization for cartilage tissue engineering." Acta biomaterialia 7.1 (2011): 234-243.
Yoo, Hyuk Sang, et al, "Surface-functionalized electrospun nanofibers for tissue engineering and drug delivery." Advanced drug delivery reviews 61.12 (2009): 1033-1042.
Notice of Allowance dated Jun. 24, 2014 in counterpart Korean Application No. KR 10-2014-0014770 (5 pages, in Korean).

* cited by examiner

FIG. 1A
FIG. 1B
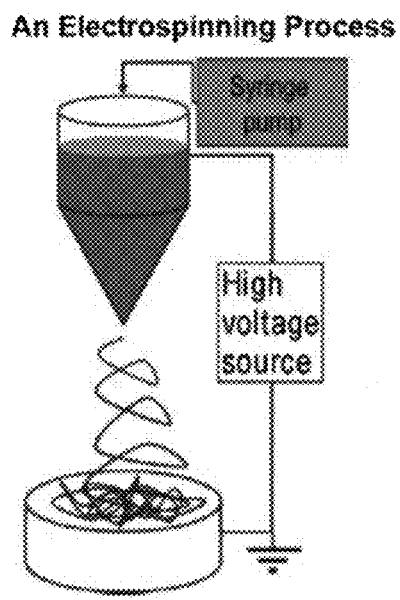
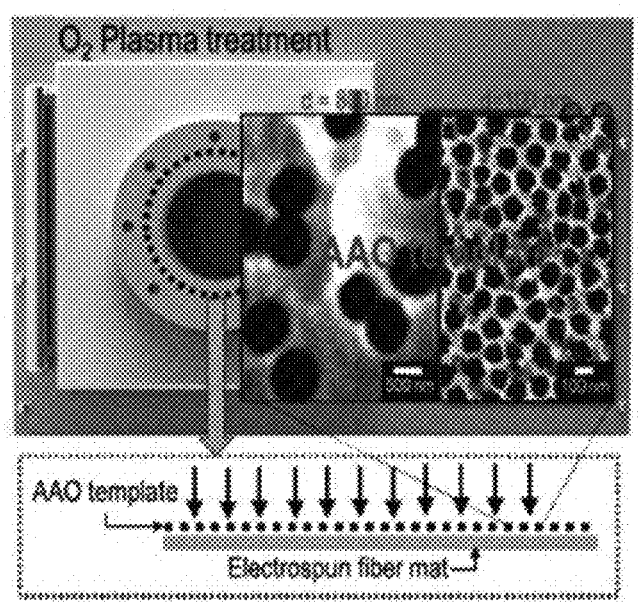

SURFACE MODIFIED POLYMERIC NANOFIBER SUBSTRATES BY PLASMA TREATMENT AND FABRICATION PROCESS FOR THE SAME

CROSS-REFERENCE TO RELATED APPLICATIONS

This application claims under 35 U.S.C. § 119(a) the benefit of Korean Patent Application No. 10-2014-0014770 filed Feb. 10, 2014 in the Korean Intellectual Property Office, the disclosure of which is incorporated herein by reference in its entirety for all purposes.

BACKGROUND

1. Field of the Invention

The present invention relates to a method of modifying a surface of a polymeric nanofiber, for example, a polymeric nanofiber mat, by modified plasma treatment, and a polymeric nanofiber having a structurally nanopatterned surface obtained using the method.

2. Discussion of Related Art

In recent years, as nano-imprinting technology have attracted much attention as one of next-generation lithographic processes, lots of research institutions and organizations have paid attention have taken active interests in fabrication and application of nanopatterns using such technology. With the development of nano-patterning technology, it is possible to manufacture a substrate having a nanopattern, or a micro-nano hybrid pattern. In this case, representative patterning technology used to manufacture the substrate includes soft lithography, UV lithography, plasma lithography, thermal lithography, etc. Particularly, plasma lithography is one of patterning methods which have paid current attention since they can be used to physically and chemically surface-modify a surface of the substrate.

However, conventional polycaprolactone (hereinafter abbreviated as 'PCL') microfiber patterning using plasma may be performed to provide nano-sized roughness and hydrophilic properties. However, the conventional PCL microfiber patterning has a problem in that it is difficult to pattern PCL into a certain nano-sized morphology due to the high working temperature upon plasma treatment since PCL is melted at a certain temperature. Further, PCL polymers widely used as biopolymers has a limitation in that they are sensitive to the temperature, and thus materials may be melted to collapse a fiber morphology when high power is applied to enhance plasma treatment efficiency (see Yan D. et al., J. Biomed. Mater. Res. Part A 2013, 101, 963-72; Nandakumar A. et al., Biofabrication, 2013, 5, 015006-015020).

Also, when plasma treatment is performed at low power to avoid a high working temperature upon patterning, plasma treatment efficiency may be degraded, which makes it difficult to effectively perform the patterning [Nandakumar A. et al., Biofabrication, 2013, 5, 015006-015020].

Meanwhile, in the tissue engineering, biomedical scaffolds requires various physical and biological properties, as follows: (1) supporting a structure to induce attachment, proliferation, and differentiation of seed cells, (2) mechanical properties substantially similar to innate tissue surrounding the scaffolds, (3) a physical clue, for example, topography inducing cell attachment to a binding site, (4) a mechanism for transferring a growth factor, and (5) a porous microstructure enabling diffusion of nutrients and exchange of metabolites inducing angiogenesis.

Various synthetic materials used to fabricate a scaffold for tissue regeneration, which has the above-described properties, have been proposed. By way of example, the synthetic materials may include polycaprolactone (PCL), poly(lactic acid) (PLA), poly(glycolic acid) (PGA), poly(lactic acid-co-glycolic acid) (PLGA), and the like, and natural materials may, for example, include collagen, alginic acid, silk fibroin, chitosan, gelatin, and the like. Among such biocompatible materials, PCL has been widely researched for wide applicability in hard tissue regeneration due to biocompatibility, slow biodegradability, structural solidity, controllable mechanical properties, and processability.

However, PCL has low bioactivity due to the lack of hydrophobic bio-functional groups on a surface thereof. As a result, the growth rate of tissues is delayed by lowering an initial cell affinity of PCL and reducing cellular interactions.

For these reasons, a surface modification of PCL has been used as a tool for improving bioactive properties of synthetic PCL scaffolds. Typical surface modification methods may include chemical treatment, laser treatment, ion beam irradiation, and plasma treatment.

Among these methods, plasma treatment has excellent probability since it does not have an influence on bulky mechanical properties of the materials.

Further, in plasma treatment, a harmful toxic solvent that may remain on a surface of a material and cause damage to seed cells is not used. Also, a variety of gases used for plasma discharge may act as cell binding sites on a modified PCL surface. Therefore, the plasma treatment is one of the most attractive processes in the field of bio-fabrication.

Habibovic, et al. reported that, when electrospun fibers made of a poly(ethylene terephthalate)/poly(butylene terephtalate)(PET/PBT) copolymer are exposed to radio-frequency oxygen plasma, plasma-treated scaffolds have a positive effect on differentiation of osteoblasts in human mesenchymal stromal cells (hMSCs) (see A. Nandakumar, Z. T. Birgani, D. Santos, A. Mentink, N. Auffermann, K. van derWerf, M. Bennink, L. Moroni, C. van Blitterswijk and P. Habibovic, Biofabrication, 2013, 5, 015006j.).

Another research by Sun, et al. reported that rapid-prototyped PCL is treated with plasma for different periods of time, and significant differentiation of osteoblasts, secretion of osteocalcin proteins, and calcium mineralization are observed on a surface of PCL after 3 minutes of plasma treatment, as evaluated by alkaline phosphatase (ALP) activities (see E. D. Yildirim, D. Pappas, S. Guceri and W. Sun, Plasma Processes Polym., 2011, 8, 256.). Such results indicate that the use of optimized plasma exposure time may cause differentiation of 7F2 mouse osteoblasts.

As pointed out by Habibovic, et al., however, the plasma treatment for surface modification is effective, sample and inexpensive, but has some problems. In particular, the plasma treatment has a problem in that it is difficult to control the size of a surface pattern of PCL with high resolution.

The conventional technology of modifying a surface of a PCL microfiber using plasma is useful in giving low roughness and hydrophilicity, but has problems in that materials are restrictive due to a high working temperature, and desired topography and roughness may not be obtained due to a decrease in plasma treatment efficiency when a process is performed at low power.

SUMMARY OF THE INVENTION

The present invention is directed to a method of surface-modifying a polymeric nanofiber which is a relatively simple process method unlike conventional surface modification methods using plasma treatment and is unable to be restricted to materials of a polymeric nanofiber to be treated with plasma.

Also, the present invention is directed to a method of surface-modifying a polymeric nanofiber capable of enhancing surface modification efficiency even when tasks are done with low power during a plasma treatment process and ultimately preventing deformation of the surface-modified polymeric nanofiber or collapse of a pattern morphology when the tasks are done at a low working temperature.

In addition, the present invention is directed to a method of surface-modifying a polymeric nanofiber capable of modifying a selective portion of a surface to be modified by plasma treatment rather than the entire surface.

Further, the present invention is directed to a method of surface-modifying a polymeric nanofiber, which is more useful for a polymeric nanofiber which is vulnerable to modification and deformation of biomaterials since surface modification is performed with high efficiency while surface treatment is performed in a low frequency range in which generation of heat may be reduced.

Also, the present invention is directed to a method of surface-modifying a polymeric nanofiber capable of easily controlling a modification area to be treated with plasma and also controlling the size of surface modification.

The present invention is directed to a surface-modified polymeric nanofiber whose surface is selectively partially modified to show hydrophilicity and which has a roughened surface.

The present invention is directed to a scaffold capable of providing an apparent environment in which target cells may grow well to an engrafted site, thereby resulting in a rapid regenerative ability and shortening of a treatment period of time.

However, the technical objects of the present invention are not limited thereto, and other objects of the present invention which are not disclosed herein will become more apparent to those of ordinary skill in the art by describing in detail exemplary embodiments thereof.

According to an aspect of the present invention, there is provided a method of surface-modifying a polymeric nanofiber using plasma treatment. Here, the plasma treatment is performed in a state in which an anodic aluminum oxide template is placed on the polymeric nanofiber.

According to one exemplary embodiment, the polymeric nanofiber may be a polymeric nanofiber mat.

According to one preferred exemplary embodiment, the polymeric nanofiber may include at least one selected from the group consisting of polycaprolactone (PCL), poly(lactic acid) (PLA), poly(glycolic acid) (PGA), poly(lactic acid-co-glycolic acid) (PLGA), and a mixture thereof.

According to the most preferred exemplary embodiment, the polymeric nanofiber may include polycaprolactone (PCL).

According to one preferred exemplary embodiment, the plasma treatment may be low-frequency oxygen plasma treatment.

According to one specific exemplary embodiment, the plasma treatment may be performed for 120 minutes to 240 minutes under conditions of a frequency of 50 kHz, a power of 10 to 30 W, an oxygen flow rate of 10 to 15 sccm, and a pressure of $5.1 \times 10^{-1}$ to $5.4 \times 10^{-1}$ Torr.

According to another specific exemplary embodiment, the anodic oxide template may have a plurality of holes having an average diameter of 100 to 800 nm formed therein.

According to another aspect of the present invention, there is provided a polymeric nanofiber mat having a modified surface. Here, a) the modified surface includes a plurality of nanoscale patterns containing hydrophilic groups, b) the hydrophilic groups are present in a state in which the hydrophilic groups are chemically bound to polymeric nanofibers, and c) the modified surface satisfies physical properties in which a surface roughness Ra is in a range of 650 to 800 nm For the polymeric nanofiber mat according to the exemplary embodiments, the polymeric nanofibers may include at least one selected from the group consisting of polycaprolactone (PCL), poly(lactic acid) (PLA), poly(glycolic acid) (PGA), poly(lactic acid-co-glycolic acid) (PLGA), and a mixture thereof. According to the most preferred exemplary embodiment, the polymeric nanofibers may include polycaprolactone (PCL).

According to still another aspect of the present invention, there is provided a scaffold for tissue regeneration including the polymeric nanofiber obtained by the fabrication method according to the exemplary embodiments of the present invention.

According to yet another aspect of the present invention, there is provided a scaffold for tissue regeneration including the polymeric nanofiber mat according to the exemplary embodiments.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1A is a diagram schematically showing an electrospinning process, and FIG. 1B is a diagram schematically showing a process of performing plasma treatment in the presence of an AAO template according to one exemplary embodiment of the present invention;

Figure 6:
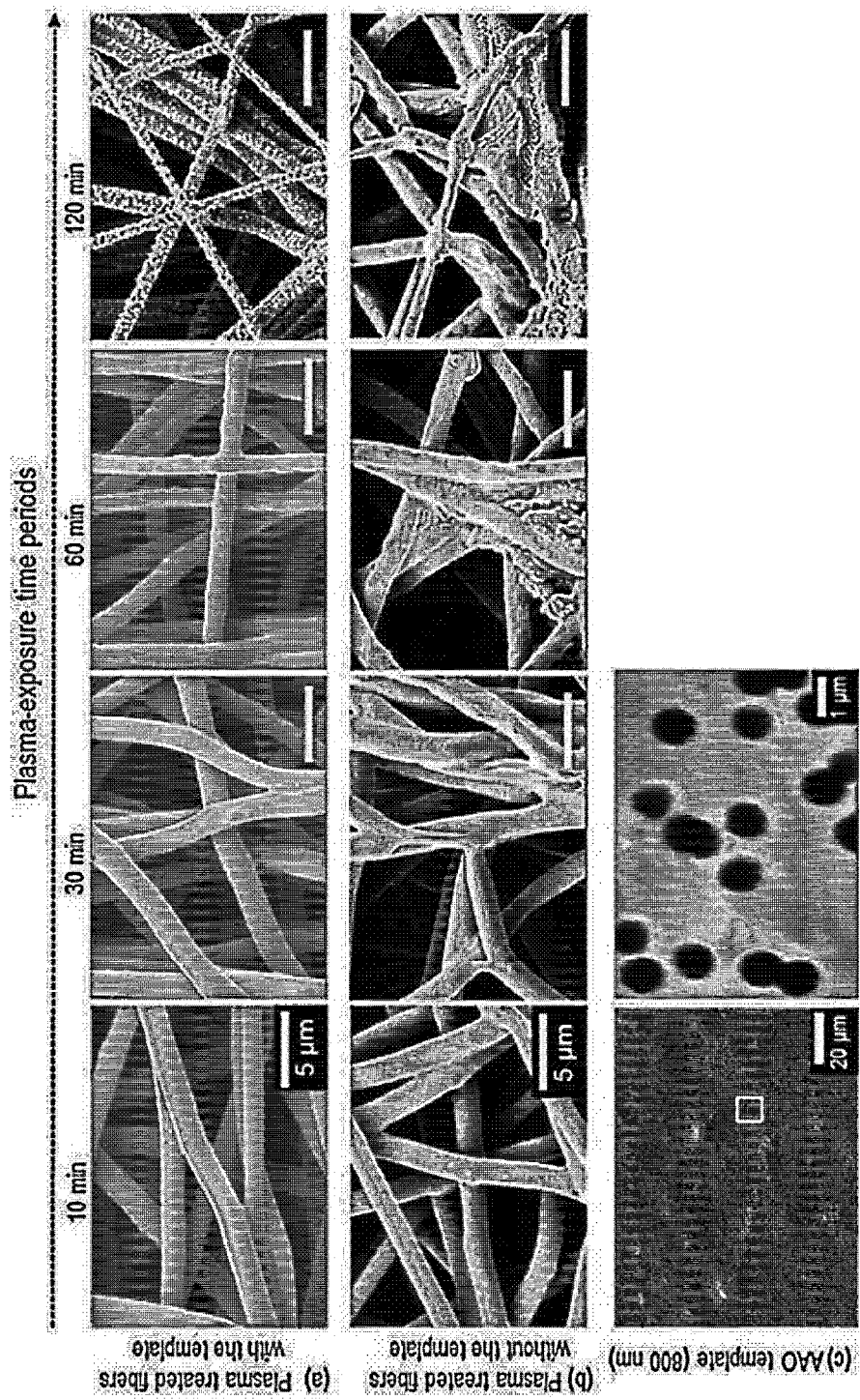
Figure 7:
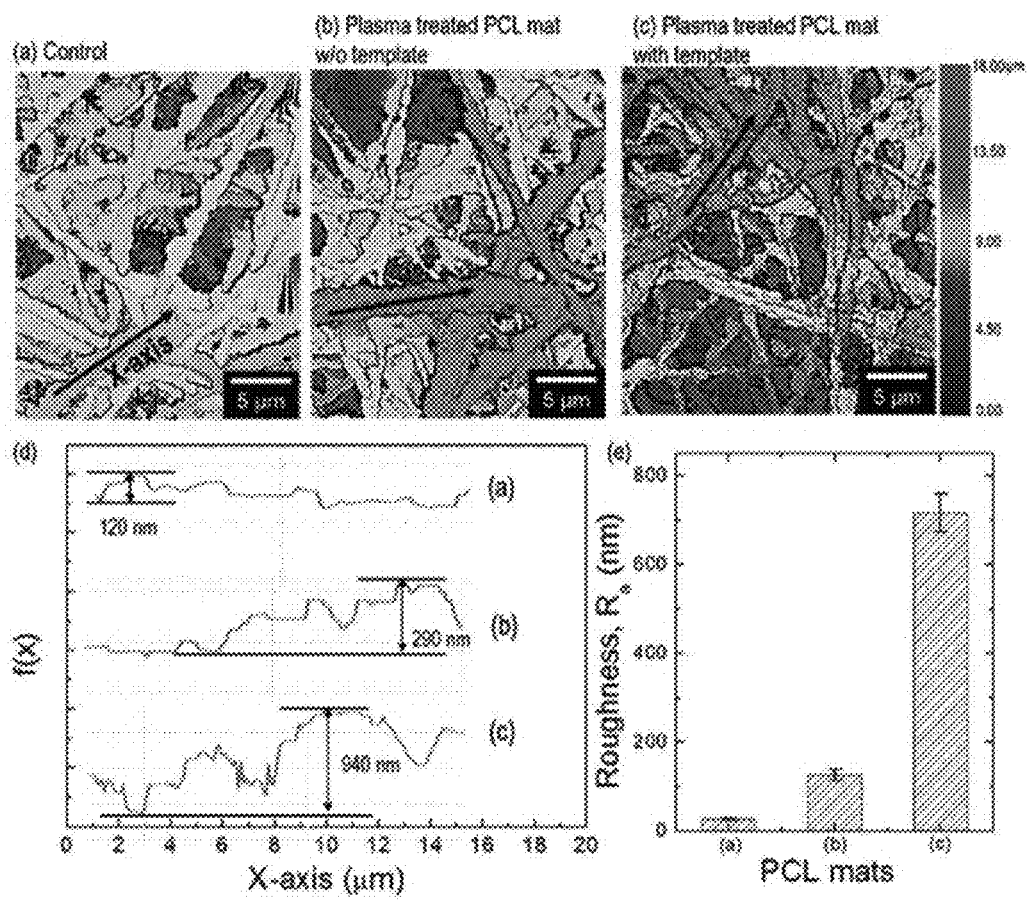
Figure 8:
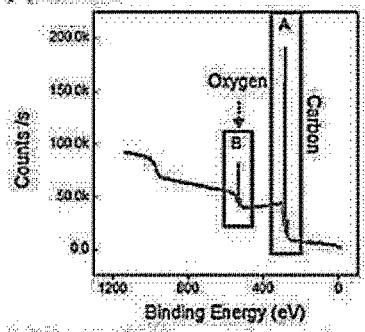
Figure 8:
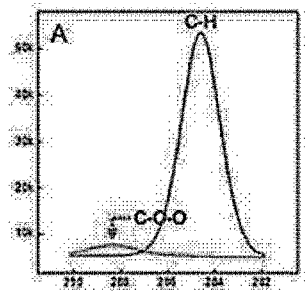
Figure 8:
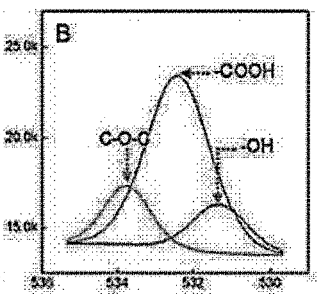
Figure 8:
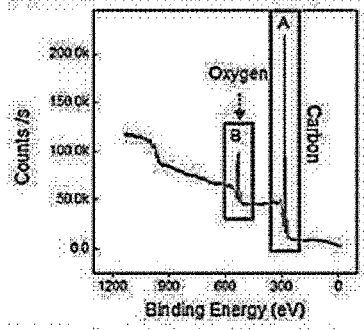
Figure 8:
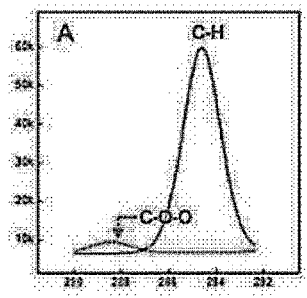
Figure 8:
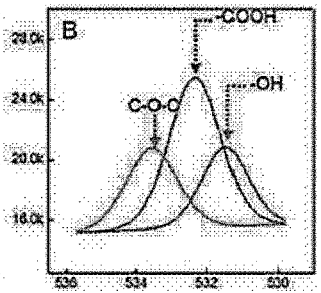
Figure 8:
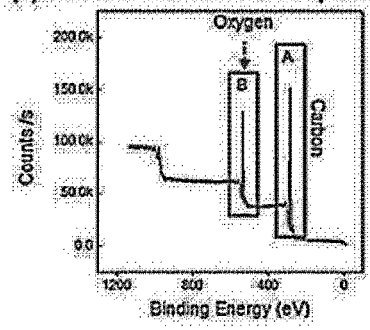
Figure 8:
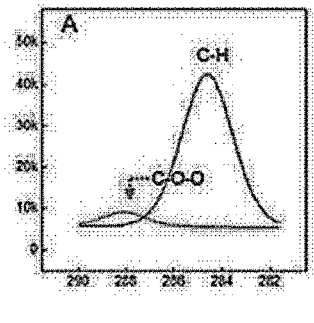
Figure 8:
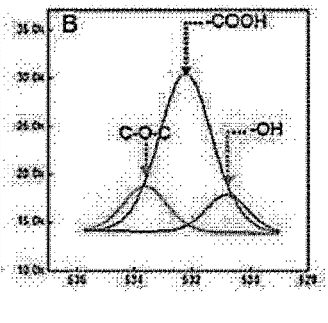
Figure 9:
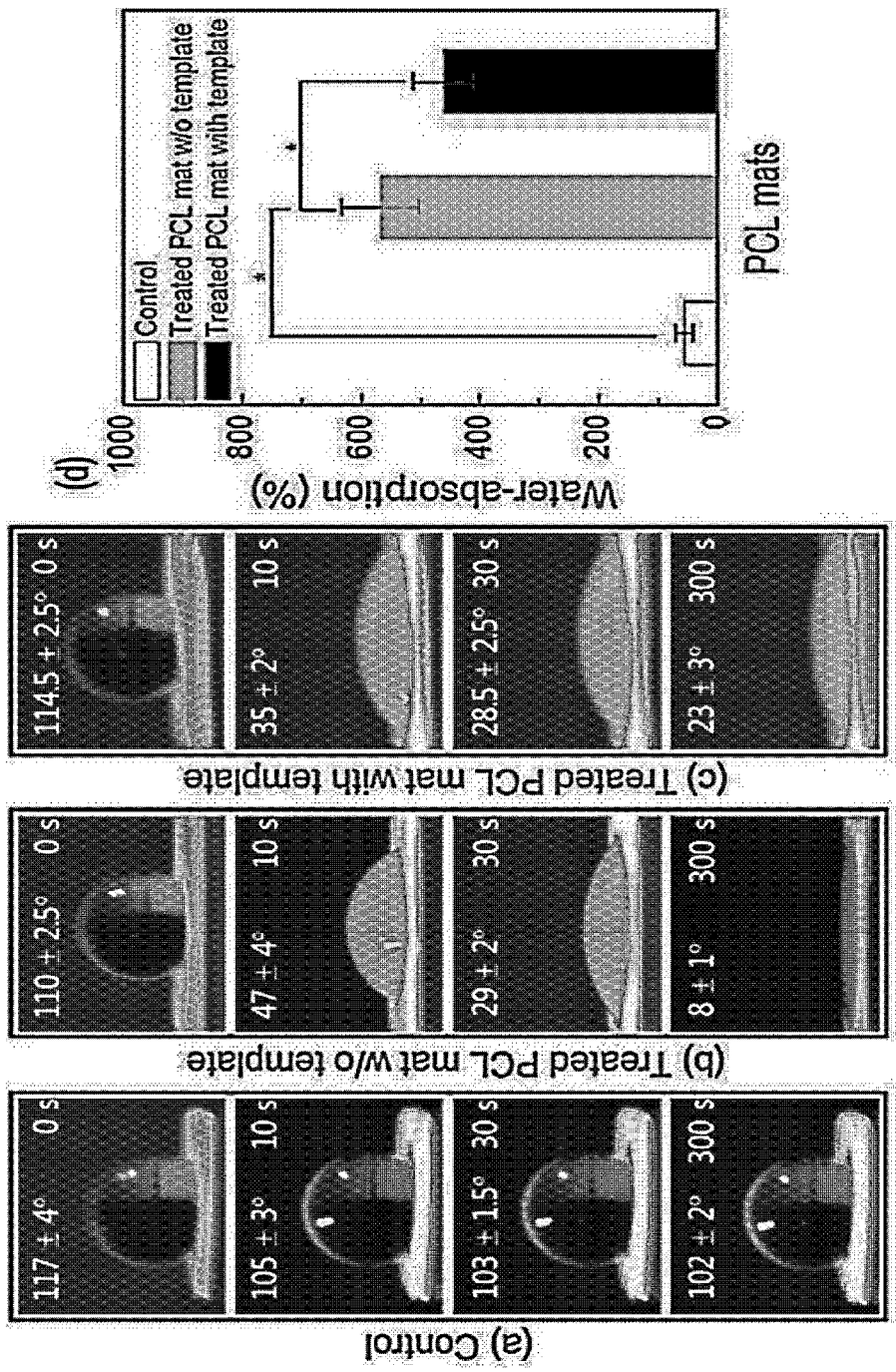
Figure 10B:
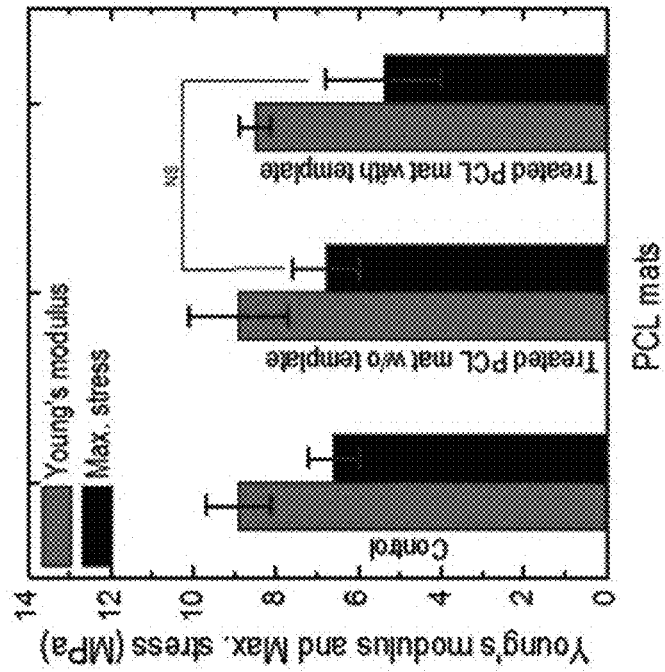
Figure 10A:
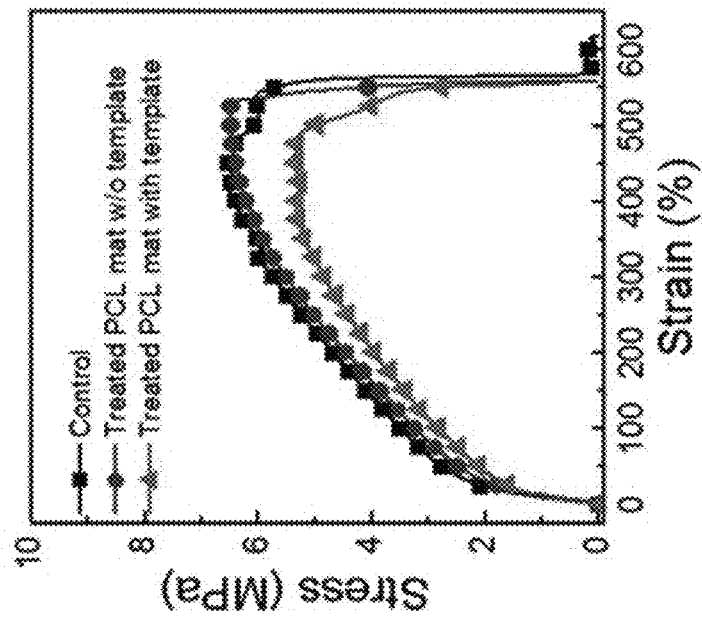
Figure 11:
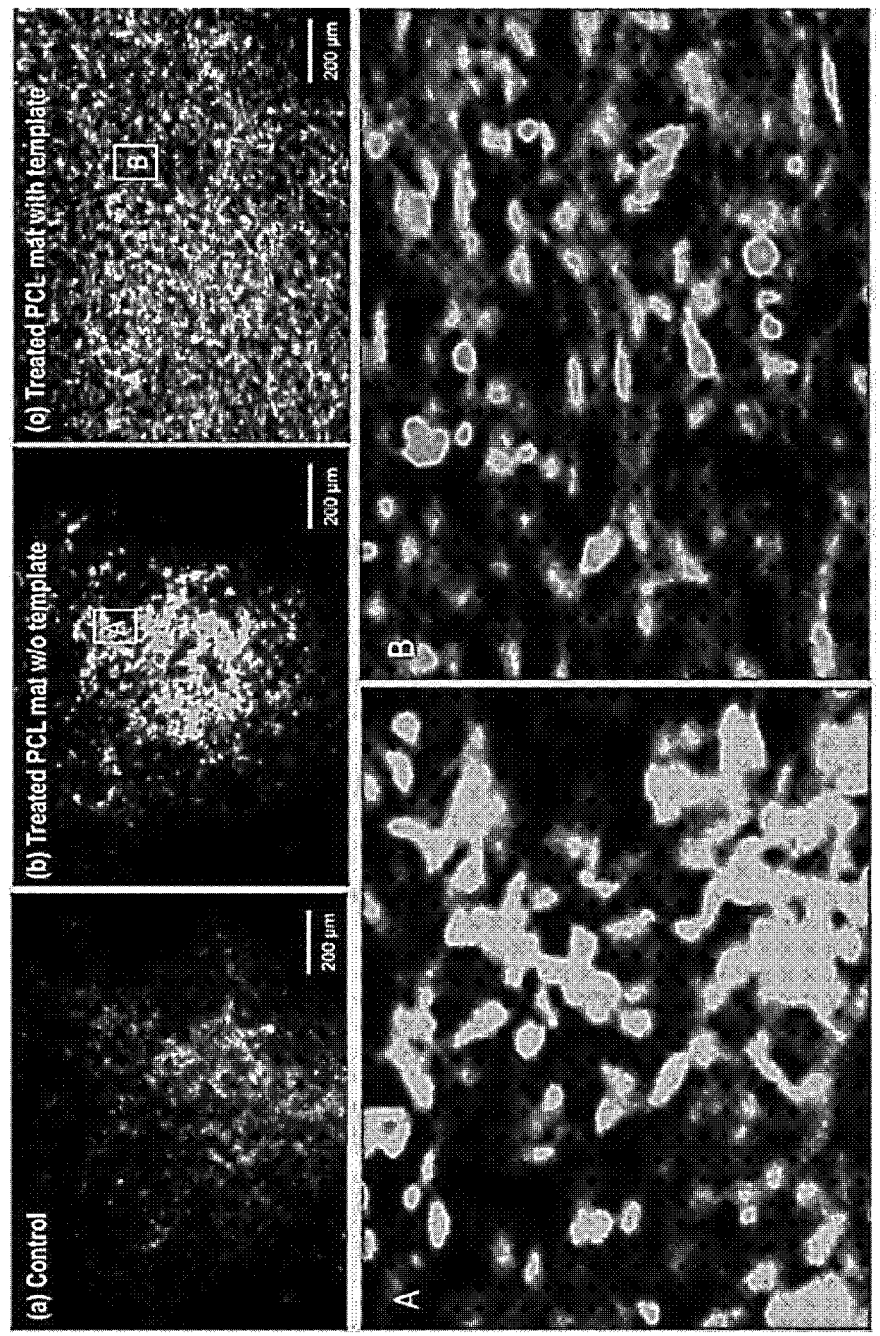
Figure 12:
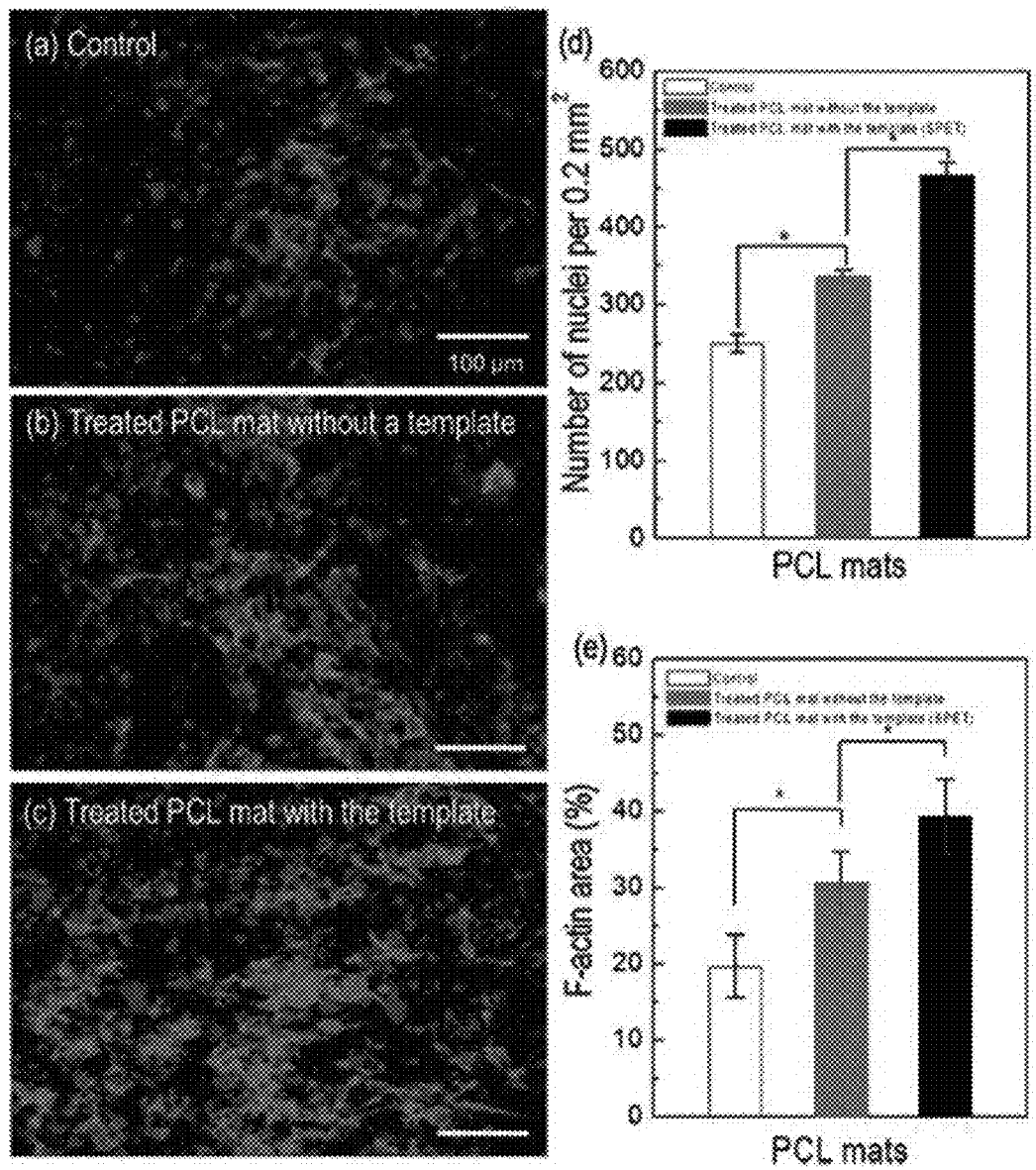
Figure 13:
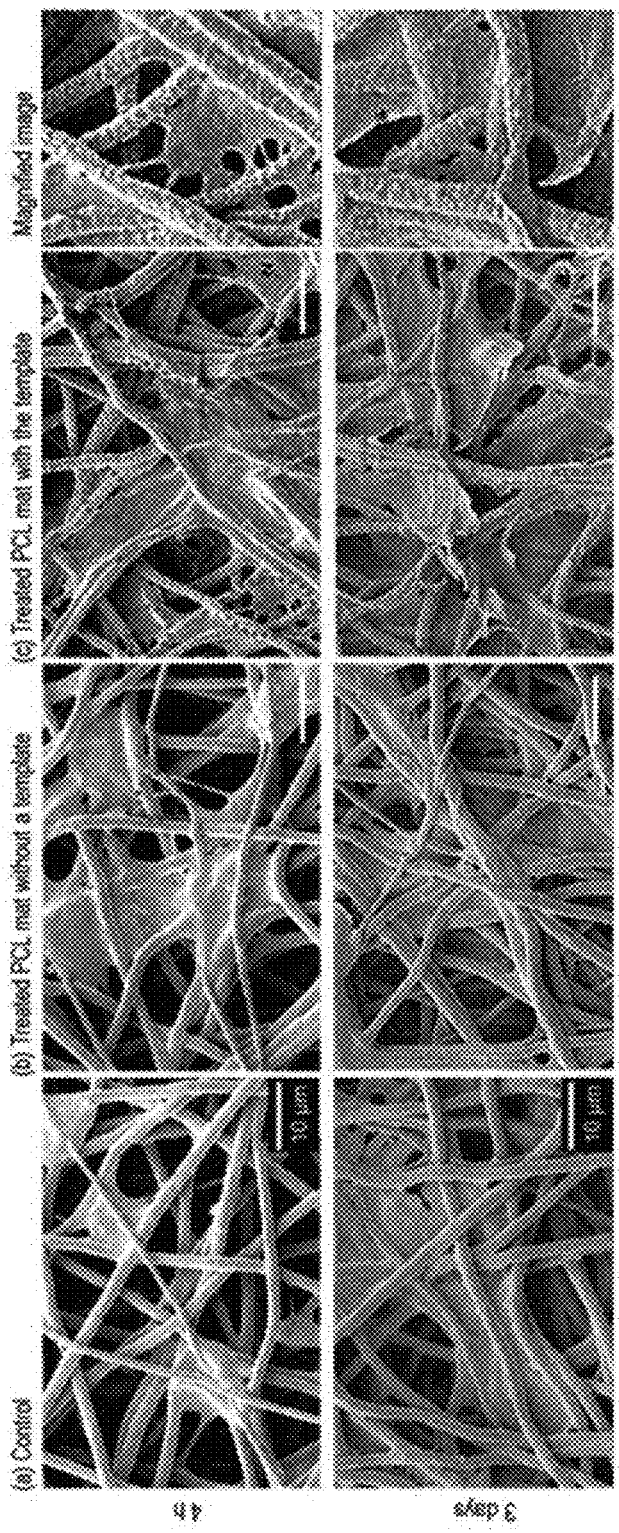
Figure 14:
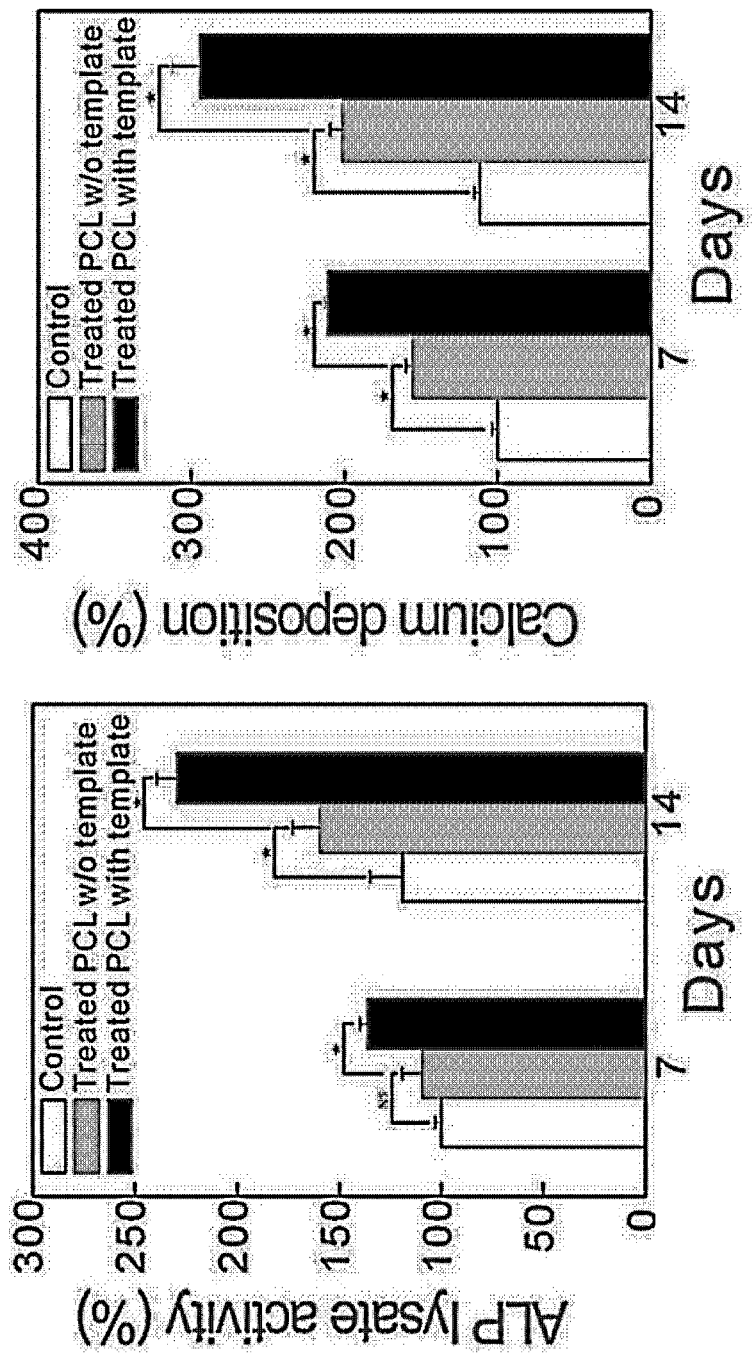
Figure 13:
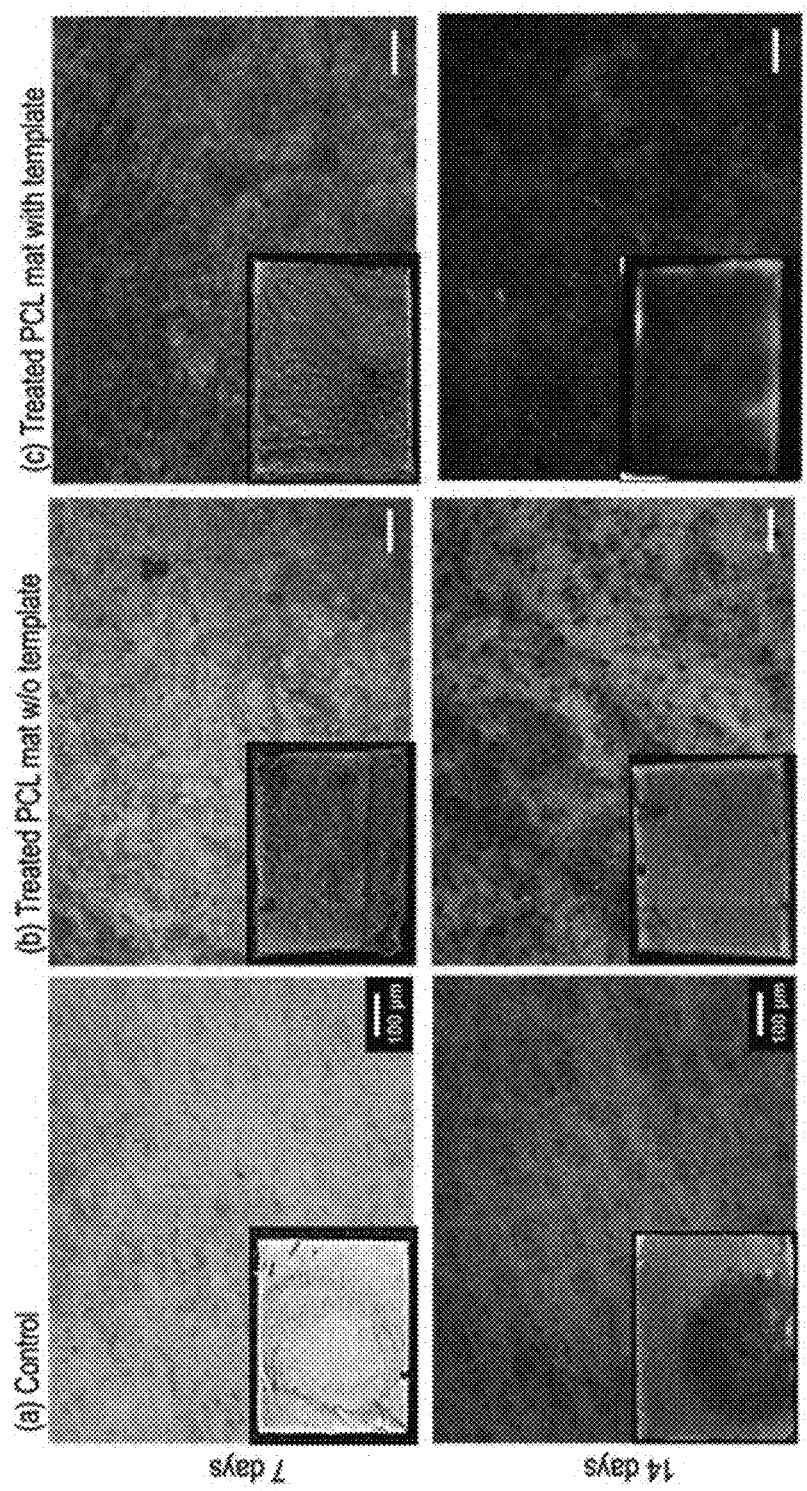

fluorescence spectrometry images of an F-actin area after the 4 hour and 24 hour cultures, where these data are indicated by an average±standard deviation (n=30), and * represents a significant difference;

FIG. 6 are SEM images of the morphology of surfaces of electrospun fibers exposed for various periods of time: (A) fibers treated with plasma (a plasma power of 10 W, and an oxygen flow rate of 10 sccm) in the presence of an 800 nm AAO template, (b) fibers treated with plasma in the absence of the template under the other same conditions, and (c) an 800 nm AAO template;

FIG. 7 are 3D topographic images of (A) the control, (B) a PCL mat treated with plasma in the absence of a template, (C) a PCL mat treated with plasma in the presence of the template, (D) 3D profiles of roughened surfaces, and (e) average roughness(Ra) of specimens;

FIG. 8 is a diagram showing the XPS results of (A) the control (an untreated PCL mat), (B) a surface of a PCL mat treated with plasma in the absence of a template, and (C) a surface of the PCL mat treated with plasma in the presence of the template;

FIG. 9 are images of contact angles of one droplet(10μl) of water mixed with a red dye with respect to (A) the control, (B) a PCL mat treated with plasma in the absence of a template, and (C) a PCL mat treated with plasma in the presence of the template, and FIG. 9D is a graph (right panel) showing comparison of water absorptions (%) of various PCL mats after 2 hours (n=5);

FIG. 10A is a stress-strain curve plotted for specimens, and FIG. 10B is a graph showing the results obtained by comparing the Young's moduli and maximum stresses of PCL mats (n=5), where 'NS' represents a non-significant difference;

FIG. 11 are images showing live (green) and dead (red) MG63 cells after the cells are cultured on respective PCL mats for 4 hours: (A) the control, (B) a PCL mat treated with plasma in the absence of a template, and (C) a PCL mat treated with plasma in the presence of the template;

FIG. 12 are DAPI/phalloidin images after the cells are cultured on the respective PCL mats for 3 days: (A) the control, (B) a PCL mat treated with plasma in the absence of a template, (C) a PCL mat treated with plasma in the presence of the template, (D) the number of the cell nuclei, and (E) an F-actin area after cultured for 3 days, where these data are indicated by an means ±standard deviation, and*represents a significant difference;

FIG. 13 are SEM images of PCL fibrous mats when the cell are cultured for 4 hours and 3 days: (A) the control, (B) a PCL mat treated with plasma in the absence of a template, and (C) a PCL mat treated with plasma in the presence of the template;

FIG. 14 is a graph showing ALP activities of MG63 cells cultured for 7 days and 14 days in the control, a PCL mat treated with plasma in the absence of a template, and a PCL mat treated with plasma in the presence of the template (right), and a graph showing calcium deposition on the specimens (left); and FIG. 15 are optical images stained with Alizarin Red S (ARS) of (A) the control, (B) a PCL mat treated with plasma in the absence of a template, and (C) a PCL mat treated with plasma in the presence of the template after the cells are cultured for 7 days and 14 days.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

In the method of surface-modifying a polymeric nanofiber according to one exemplary embodiment of the present invention, the term 'polymeric nanofiber' will be understood as a fiber having nano-sized pores and a diameter, which is obtained from a spinning solution including a polymer using a typical method such as electrospinning That is, the polymeric nanofiber includes a nanofiber mat, which is obtained by dissolving a polymer in a solvent and electrospinning the resulting solution at a high voltage.

The method of surface-modifying a polymeric nanofiber according to one exemplary embodiment of the present invention is a method of surface-modifying a polymeric nanofiber by plasma treatment. In this case, the plasma treatment is characterized in that it is performed in a state in which an AAO template is placed on the polymeric nanofiber.

The AAO template is obtained by subjecting an aluminum layer to an anodic oxidation process to form a plurality of holes. In this case, the diameter and depth of the formed holes may be adjusted according to the conditions for the anodic oxidation process.

In the present invention, a surface of a specimen to be modified is selectively modified by subjecting such an AAO template to plasma treatment in a state in which the AAO template is placed on the specimen.

When the AAO template is introduced for the plasma treatment, the specimen may be treated to have a surface modified with a nano-sized morphology and roughness.

Generally, the surface modification by plasma treatment is a method of surface-modifying an entire surface of a specimen to be modified, but has problems in that a surface structure of a polymer such as PCL may be damaged, and the polymer itself may deteriorate due to the overall surface modification. In this point of view, the conventional surface modification by plasma treatment is not desirable for the polymer, such as PCL, which is very sensitive to the temperature. According to the present invention, as the nanoscale patterns may be structurally formed since the specimen may be surface-modified to a selective area corresponding to the area of the holes formed in the AAO template, the surface modification may be performed on the specimen so that the specimen has a surface having much higher roughness than that modified through the normal plasma treatment.

Further, such selective modification may be realized at a low frequency band. By way of example, a surface of the polymeric nanofiber may be effectively modified by low-frequency oxygen plasma treatment.

Specifically, the surface of the polymeric nanofiber may be sufficiently effectively modified at a low frequency band of 50 kHz by oxygen plasma treatment.

In a plasma treatment process performed at a high frequency band, heat may be generated during the treatment process. As a result, the surface of fibers may be damaged during the treatment process in the case of a processing fiber sensitive to the temperature, and may not easily surface-modified into nanopatterns.

Also, since the surface of the fibers may be structuralized without applying higher power than normal plasma treatment methods, the surface modification is possible so that the fibers have modified structural properties and hydrophilic properties. In this case, the effective surface modification is possible in a power range of 10 to 30 W. Such a power range is a range in which a small amount of heat is generated. When the plasma power is greater than the power range, the nanofibers on the polymeric nanofiber may be melted.

When the plasma treatment is performed at the above-described low frequency band and power ranges for at least 120 minutes, preferably 120 minutes to 240 minutes, it is possible to obtain a surface-modified surface significantly patterned at a nanoscale. Realizing the plasma exposure time within this range may also be considered to be due from the use of the AAO template. Even when a processing specimen is exposed to plasma for a long period of time, a negative effect is not exerted on the processing specimen. Therefore, a plasma treatment time may be further lengthened, resulting in more robust chemical bonding of hydrophilic groups to the surface of the fibers.

In addition, when the oxygen flow rate may be in a range of 10 to 15 sccm, and the pressure may be in a range of $5.1 \times 10^{-1}$ to $5.4 \times 10^{-1}$. Torr, the nanoscale patterns may be formed well.

When the plasma treatment is performed within these oxygen flow rate and pressure ranges, the normal plasma treatment (plasma treatment in the absence of the AAO template) has problems in that the surface of nanofibers to be modified may be damaged, and melted, thereby making it impossible to obtain the nanofibers having a nanoscale patterned surface.

According to the present invention, as the effective surface modification by plasma treatment is possible under the above-described conditions, the plasma treatment has an advantage in that synthetic and natural polymers used as biomaterials may be effectively surface-modified.

In an aspect of usefulness of the present invention, the polymeric nanofiber may include at least one selected from the group consisting of polycaprolactone (PCL), poly(lactic acid) (PLA), poly(glycolic acid) (PGA), poly(lactic acid-co-glycolic acid) (PLGA), and a mixture thereof, and most preferably polycaprolactone (PCL).

Also, the present invention has an advantage in that it is possible to control the size of the AAO template to be surface-modified since an area to which plasma is transferred may be controlled by controlling the size of the holes in the AAO template.

The AAO template that may be used considering this aspect may be preferably a template having holes having an average diameter of 100 to 800 nm Such a diameter range is desirable in consideration of the pores of the polymeric nanofiber to be modified, and diameters of fibers.

When the average diameter of the holes of the AAO template is too small, modification efficiency by plasma treatment may be degraded. On the other hand, when the average diameter of the holes is too high, process advantages of the plasma treatment performed in the presence of the AAO template may be small. Also, the results in contrast to an intention of obtaining a surface-modified surface patterned at a nono-size may be obtained.

According to the fabrication method of the present invention, a polymeric nanofiber mat having a modified surface is obtained. In this case, a) the modified surface includes a plurality of nanoscale patterns containing hydrophilic groups, b) the hydrophilic groups are present in a state in which the hydrophilic groups are chemically bound to polymeric nanofibers, and c) the modified surface satisfies physical properties in which a surface roughness Ra is in a range of 650 to 800 nm The polymeric nanofiber mat having the modified surface satisfying such requirements may not be obtained by plasma treatment known in the related art. When the hydrophilic groups are introduced into the surface of the polymeric nanofiber mat by the plasma treatment, the polymeric nanofiber becomes hydrophilic. Also, the hydrophilic groups are present in a state in which the hydrophilic groups are not simply physically bound to the surface of the polymeric nanofiber but chemically bound to the surface of the polymeric nanofiber, but the modified surface of the polymeric nanofiber does not satisfy the properties in which a plurality of nanoscale patterns including hydrophilic groups are formed. That is, the surface-modified polymeric nanofiber mat according to one exemplary embodiment of the present invention has a microstructure nanoscale patterned on a surface thereof.

Also, the surface-modified polymeric nanofiber is characterized in that the roughness of the surface-modified polymeric nanofiber is high to an extent to which the roughness cannot be achieved by the normal plasma treatment. This is because that the surface modification is possible to have a pattern similar to the structure of the nano-sized holes of the template when the plasma treatment is performed in the presence of the AAO template. Therefore, the modified surface may satisfy the surface properties in which the surface roughness Ra is in a range of 650 to 800 nm The surface-modified polymeric nanofiber satisfying such surface properties may be used as a scaffold, and may provide an apparent environment in which target cells may grow in an engrafted site when a patient is engrafted with the surface-modified polymeric nanofiber, thereby resulting in a rapid regenerative ability and shortening of a treatment period of time.

Hereinafter, preferred embodiments are presented to aid in understanding the present invention. However, it should be understood that detailed description provided herein is merely intended to provide a better understanding of the present invention, and not to limit the scope of the present invention.

In Examples provided herein, to check the superiority of the method of surface-modifying a polymeric nanofiber using plasma and an anodic aluminum oxide (AAO) template according to one exemplary embodiment of the present invention, an example in which a nanoscale structure is patterned on a surface of the PCL nanofiber mat is provided. However, it should be understood that such an example provided herein is not intended to limit the processing polymeric nanofiber itself to which the method of surface-modifying a polymeric nanofiber according to one exemplary embodiment of the present invention is applied.

The method of surface-modifying a polymeric nanofiber according to one exemplary embodiment of the present invention is selective for a processed area in the plasma treatment, and also has various selectivities to a surface-modified portion by controlling the size of the holes in the AAO template. In such aspects, the method of surface-modifying a polymeric nanofiber according to one exemplary embodiment of the present invention is used under the name of 'selective plasma-exposure treatment (hereinafter abbreviated as 'SPET').

PREPARATIVE EXAMPLE 1

FIG. 1A is a diagram schematically showing an electrospinning process.

To fabricate a fibrous mat, poly(ε-caprolactone) (PCL, Mw=90,000, Aldrich) was used as a material, and n,n-dimethylformamide (DMF, JUNSEI) and methylene chloride (MC, JUNSEI) were mixed as solvents at a ratio of 4:1 to prepare a PCL polymer solution, which was then spun at a content of 10 wt %. As a result, it could be seen that the microfibers were homogenously fabricated, as determined by SEM.

To fabricate the PCL nanofiber mat, a high-voltage power supply (SHV300RD-50K; Convertech, Seoul, South Korea), a syringe pump (KDS 230; KD Scientific, Holliston, Mass., USA), a collector, an auxiliary electrode, and a nozzle were used as the components of an electrospinning device. A high voltage is applied from a distance of 150 mm between the nozzle and the collector to perform spinning, and electrospinning was performed under the same conditions such as a high voltage applied to the nozzle, a distance, a period of time, etc.

The high voltage was set as 17 kV, and injection was performed at a flow rate of 0.5 mL/h with the syringe pump, and the electrospinning was performed for 30 minutes.

The temperature during the electrospinning was approximately 25° C., and the relative humidity was 38±12%.

EXAMPLE 1

(1) Plasma Treatment Method

FIG. 1B is a schematic diagram for obtaining a nanosized pattern-surface of a nonwoven fibrous mat patterned at a nano-size. In the drawing, an SPET process supplemented with 100 nm and 800 nm AAO templates is shown. Here, "d" represents an average diameter of holes in the AAO templates.

The PCL nanofiber mat fabricated using the typical electrospinning process as described in Preparative Example 1 was treated in an oxygen plasma chamber.

A plasma apparatus according to one exemplary embodiment of the present invention is composed of an LF plasma apparatus body having a generator frequency of 50 kHz, a vacuum pump configured to control a vacuum in a chamber, an oxygen tank configured to supply oxygen gas into the chamber, and an AAO template capable of enhancing surface modification efficiency and controlling the size to be surface-modified.

To modify a surface of the fabricated PCL microfiber mat, $O_2$ gas was used at a generator power, and supplied into the chamber at a flow rate of 10 sccm. In this case, this experiment is performed at a working pressure of $5.27 \times 10^{-1}$ Torr. To remove any impurities, first, the chamber was cleaned by running one cycle for 30 minutes without any sample.

As experimental groups, a total of four samples, for example, a control which was not treated with plasma at all, a sample entirely treated with plasma, and samples partially treated with plasma using AAO templates having holes having an average diameter of 100 nm and 800 nm (ANODISC FILTER, Whatman International Ltd., Maidstone, England), were fabricated.

Electrospun fibrous mats (2 cm×2 cm (a thickness of 95±13 μm)) were put into the chamber, and subjected to plasma treatment.

In the case of the sample entirely treated with plasma, when the treatment time was lengthened, the morphology of fibers might collapse due to a high working temperature. Therefore, the plasma exposure time was set to 30 minutes so that a surface of the sample was treated with plasma while maintaining the morphology of the fibers.

(2) Evaluation of Physical Properties

To characterize the morphology of a surface of the electrospun fibrous mat which was treated or not treated with plasma, SEM (SNE-3000M, Samsung Electronics Co., Ltd., KOREA) was used. Before observation, the fibrous PCL mat was sputter-coated with gold. Fabrication and measurement of specimens were performed according to the manual. After 4 hours of cell culture, an SEM image was used to perform an evaluation of morphologies (areas, perimeters, and an aspect ratio) of a single cell.

Image J software (National Institutes of Health, Bethesda, Md., USA) was used to measure an area of F-actin after the cells are cultured for 4 hours and 24 hours.

A surface roughness profile including Ra and RMS values of the fibers was measured using AFM (Nanowizard AFM, JPK Instruments, Germany). The porosity (φ) of the mat was calculated by the following Equation 1.

$$\varphi = 1 - M/(\rho h s) \qquad \text{Equation 1}$$

In Equation 1, M represents a weight of a fibrous mat, ρ represent a density (=1.145 g/cm³) of PCL, h represents a thickness of the mat, and s represents a surface area of the mat.

(3) Effect of Plasma Treatment Conditions on Patterned Surface

Since the plasma treatment conditions (a plasma exposure time, and power) might have an influence on the patterned surface, various $O_2$ plasma exposure times (10, 30, 60 and 120 minutes) and powers (10, 30, and 70 W) were used in this Example. Also, the AAO templates having holes having an average diameter of 100 and 800 nm were used to generate nanoscale patterned surfaces having different sizes.

For comparison, untreated PCL fibers, and PCL fibers treated with plasma without any template were fabricated as the control.

Figure 2A:
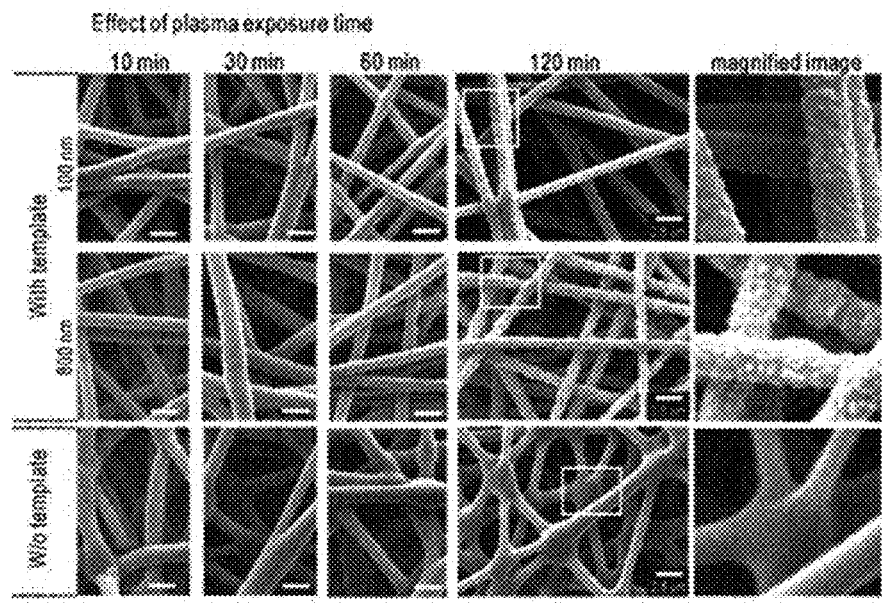
FIG. 2A is a diagram showing the results obtained by determining an effect of a plasma exposure time on topography of fibers using treatment conditions of 10 W and 10 sccm.

FIG. 2A shows an SEM image of the plasma-treated PCL fibers exposed to plasma treatment for 30, 60, and 120 minutes. The plasma power used herein was 10 W, and the oxygen flow rate was 10 sccm. The 100 nm and 800 nm templates were exposed to plasma for 120 minutes, and nanoscale patterns were sufficiently formed on the fibers. On the other hand, after the plasma treatment performed in the absence of the template, the perimeter between fibers was increasingly melted according to the plasma-exposure time. In this case, the evidence of the nanoscale patterned surface was not observed.

Figure 2B:
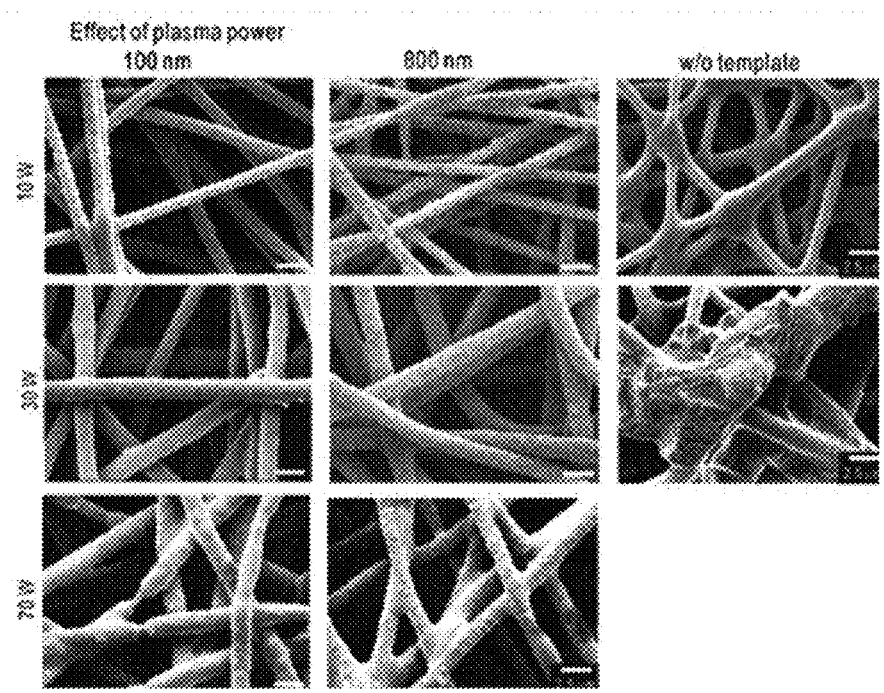
FIG. 2B is a diagram showing the results obtained by determining an effect of plasma power on the topography of the fibers using treatment conditions of 10 sccm and 120 minutes, in the form of surfaces of the fibers determined from an SEM image, where the term 'w/o template' refers to "without template;"

FIG. 2B shows an effect of plasma treatment at different plasma powers (10, 30, and 70 W) under plasma exposure for a certain period of time (120 minutes) at an oxygen flow rate of 10 sccm. Thin and neck-shaped fibers were sporadically formed at a plasma power of 70 W at which the 100 and 800 nm templates were used. On the other hand, the same templates were treated at plasma powers of 10 W and 30 W to obtain stable nanoscale patterned surfaces. However, all the exposed fibers were melted in the absence of the template at an increasing plasma power.

Also, the patterned surfaces were analyzed using AFM. The analysis results are shown in FIG. 3A to 3D.

The plasma treatment conditions were 10 W, 10 sccm, and 120 minutes in the presence of the template, and were 10 W, 10 sccm, and 30 minutes since the PCL fibers were melted in the absence of the template.

Figure 3:
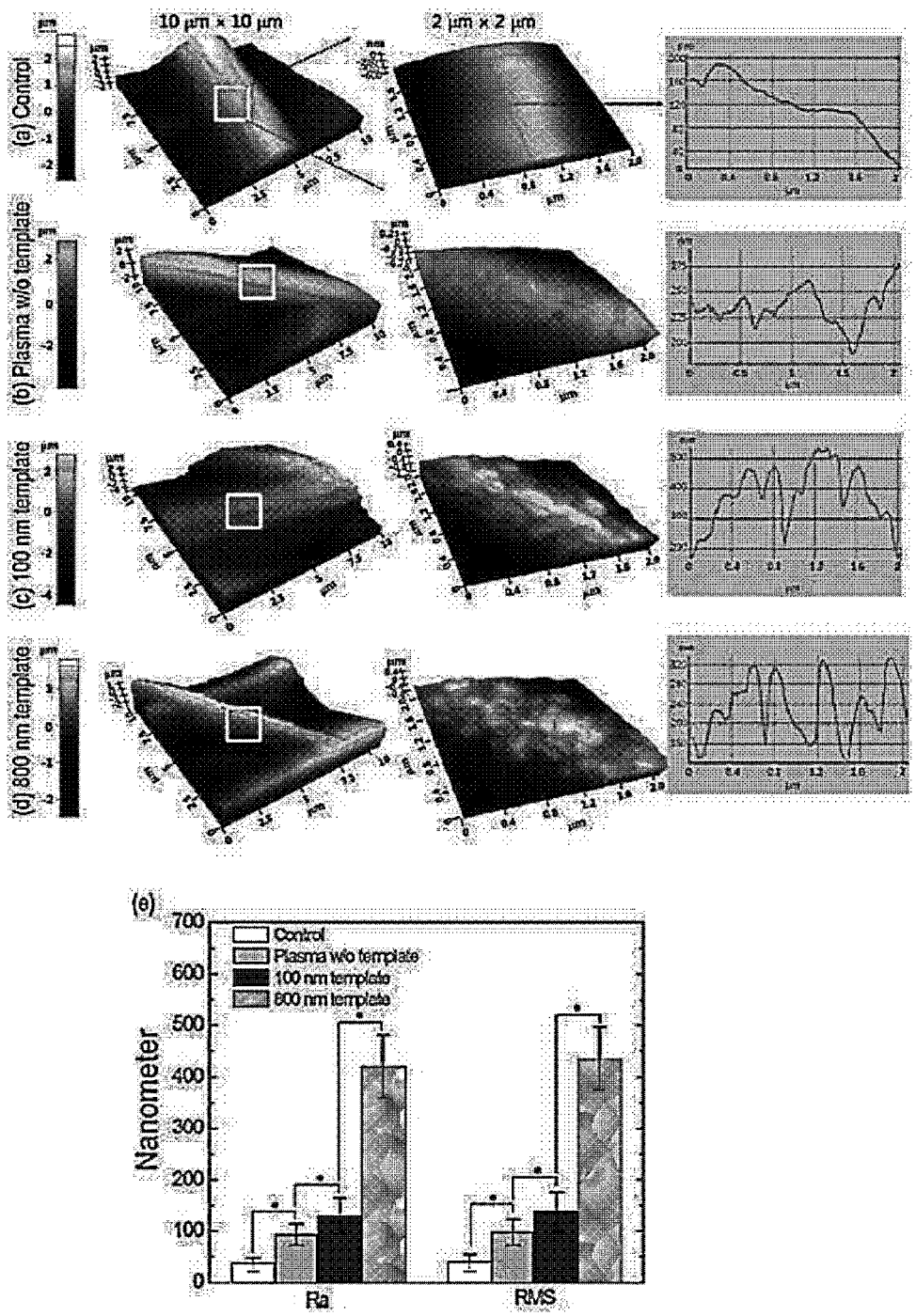
FIG. 3 is a diagram specifying surface roughness using atomic force microscopy (AFM)

The results were converted into roughness values (Ra and RMS). As shown in FIG. 3E, it was revealed that the use of the template resulted in significantly improved surface roughness of the fibers, compared to the untreated fibers and all the fibers treated with plasma without any template. This was due from the fact that plasma ions were selectively exposed to the surface of the fibers by means of the template. The fiber diameters, pore sizes, and porosities of the control and the plasma-treated fibers are listed in the following Table 1.

TABLE 1

|  | Control | W/o template | With template | |
| --- | --- | --- | --- | --- |
|  |  |  | 100 nm template | 800 nm template |
| Fiber diameter (n = 100; μm) | 3.43 ± 0.85 | 3.24 ± 0.70 | 3.29 ± 0.73 | 3.21 ± 0.63 |
| Pore size (n = 10; μm) | 25.2 ± 6.3 | 26.9 ± 7.2 | 27.2 ± 5.9 | 26.5 ± 6.9 |
| Porosity (n = 5; %) | 78.4 ± 8.6 | 80.1 ± 6.6 | 79.2 ± 7.5 | 80.3 ± 8.1 |

Figure 4:
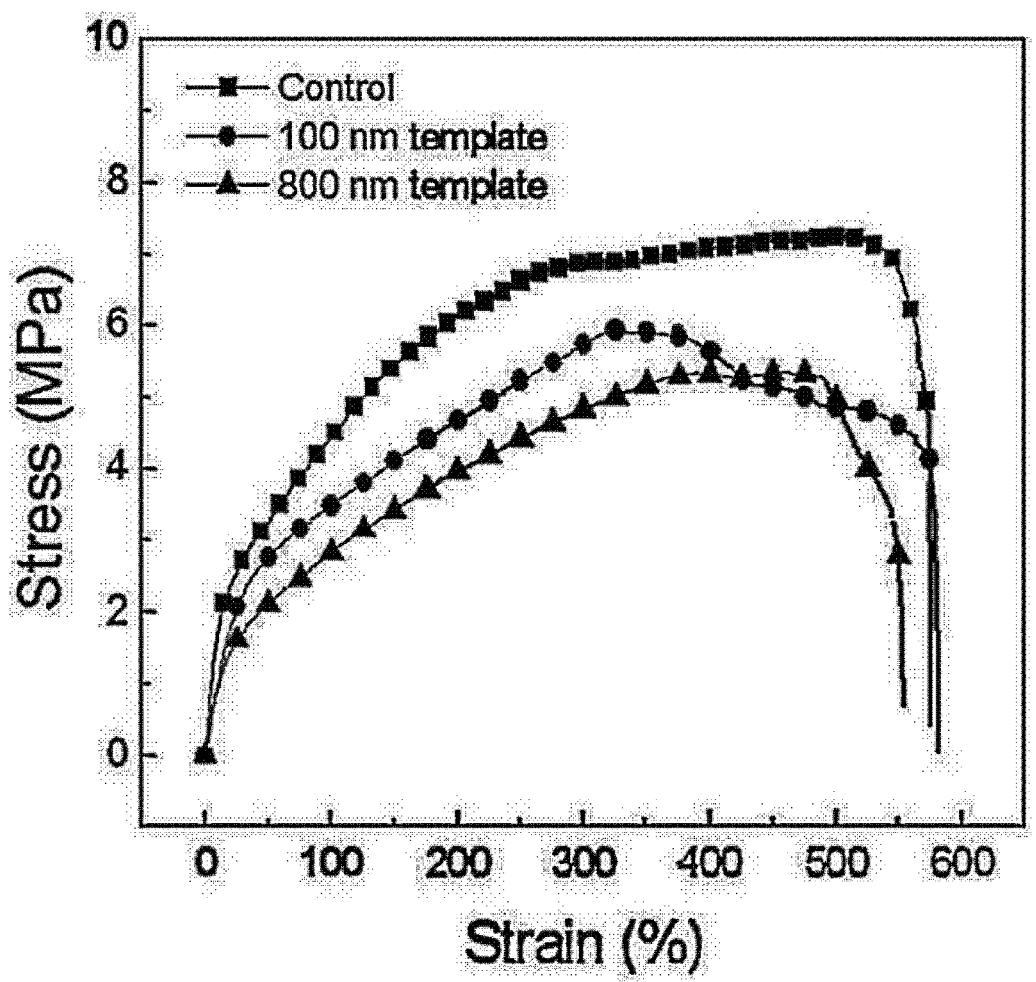
FIG. 4 is a diagram showing stress-strain curves plotted for plasma-treated fibrous mats in the presence of the control (an untreated fibrous mat) and a template (holes having an average diameter of 100 nm and 800 nm, respectively)

To measure a change in mechanical properties before and after the plasma treatment, a tensile test was also performed on the fibrous mats. FIG. 4 shows stress-strain curves plotted for the control (an untreated fibrous mat) and the fibrous mats treated with plasma in the presence of the templates (100 nm and 800 nm).

The Young's moduli of the plasma-treated PCL mats (mats treated with the 100 nm template: 8.2±0.5 MPa; and mats treated with the 800 nm template: 8.3±0.4 MPa) were slightly lower than that of the control (9.1±0.8 MPa).

The distribution (MG63) and morphology of osteoblasts on each fiber were examined using SEM and fluorescent images (DAPI and phalloidin). The results are shown in FIG. 5A (the control: an untreated fiber), FIG. 5B (PCL fibers treated with plasma in the absence of the template (w/o template plasma)), and FIGS. 5C and 5D (PCL fibers treated with plasma in the presence of the templates (100 nm and 800 nm).

Since the patterned surface might have an influence on initial cell attachment and proliferation, the observation was performed after the cells were cultured for 4 hours and 24 hours.

Typical SEM images obtained after the cells were cultured for 4 hours and 24 hours are shown in FIG. 5A to 5D.

Figure 5:
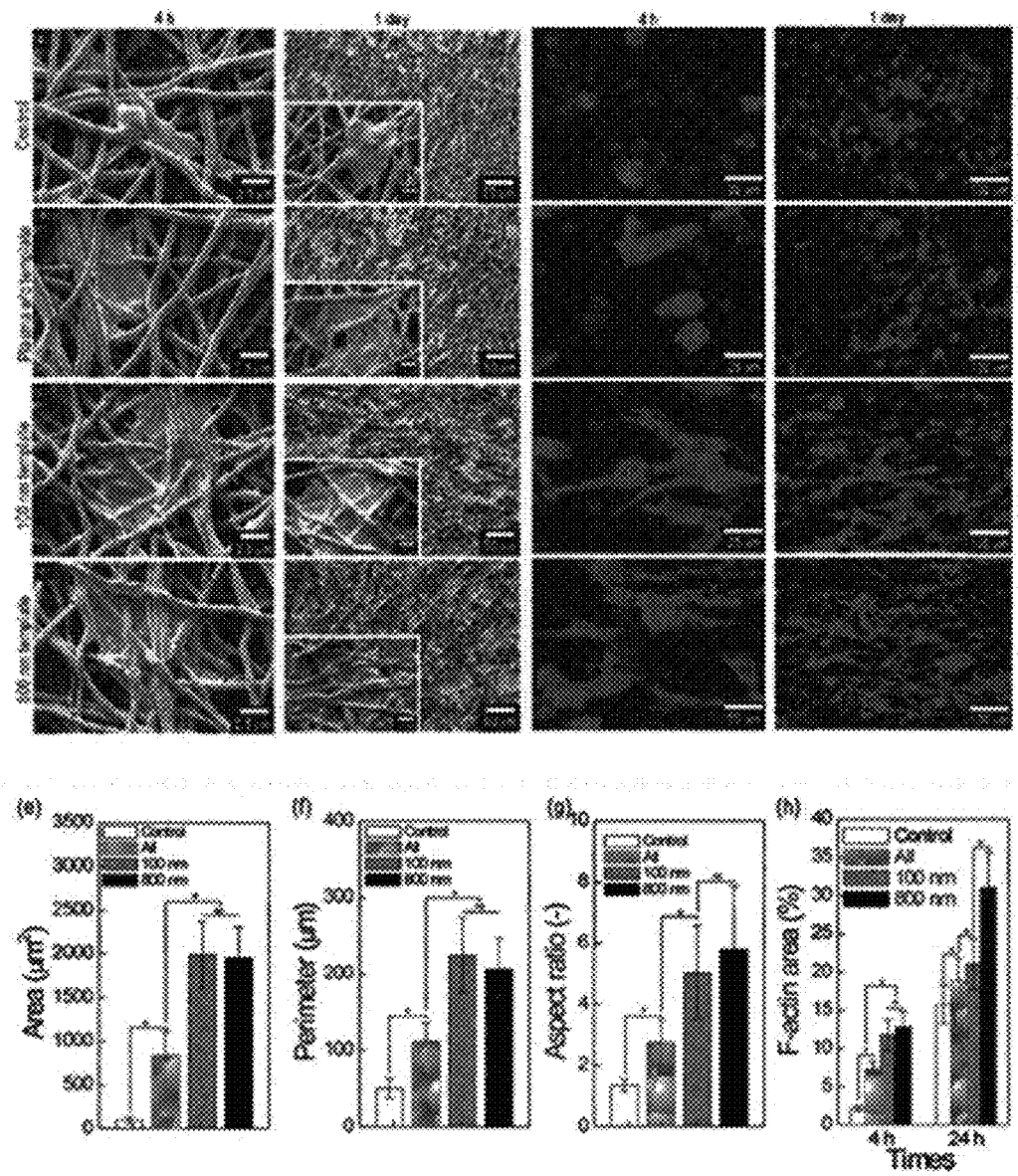
FIG. 5 are SEM and DAPI/phalloidin images after cells are cultured on fibers for 4 hours and 24 hours: (A) the control (an untreated PCL fiber), (B) PCL fibers treated with plasma (processing conditions: 10 W, 10 sccm, and an exposure time of 30 minutes) in the absence of a template, (C) PCL fibers treated with plasma (10 W, 10 sccm, and an exposure time of 120 minutes) in the presence of a 100 nm template, and (D) CL fibers treated with plasma (10 W, 10 sccm, and an exposure time of 120 minutes) in the presence of a 800 nm template, and (E) a cell area, (F) an perimeter, and (G) an aspect ratio analyzed by SEM after when MG63 cells which are being cultured on plasma-treated and untreated PCL fibers are cultured for 4 hours, and (H)

From all the SEM and DAPI/phalloidin images, the highly reinforced cell attachment and the diffusion on the nanopatterned PCL fibers were found (FIGS. 5C and 5D). As a result, it was revealed that the cells on the plasma-treated PCL fibers and the untreated fibers showed different attachment behaviors and morphologies. The cells were easily adhered onto and diffused on the plasma-treated PCL fibers having a nanoscale pattern.

However, the untreated PCL fibers showed very low cell attachment. Also, a lot of the cells were not observed on the plasma-treated PCL in the absence of the template.

FIGS. 5E to 5G show the area, perimeter, and aspect ratio after the cells are cultured for 4 hours.

The cells on the surface of the fibers treated with plasma in the presence of the template showed significantly wider diffusion area, much higher perimeter and higher aspect ratio than the control and the cells on the surface of the fibers treated with plasma in the absence of the template.

Therefore, the highly roughened surface of fiber promoted wider diffusion and more stretched morphology of the MG63 cells, thereby inducing proliferation of the cells showing the wider diffusion. The results were matched with the changes in area of F-actin at a time points of 4 hours and 24 hours well, which indicated the cell proliferation (FIG. 5H).

The highly roughened PCL fibers (treated with plasma in the presence of the 800 nm template) showed the highest level of cell proliferation. Such research results were matched with the previous reports well (see H. Lee, S. Ahn, H. Choi, D. Cho, G. H. Kim, J. Mater. Chem. B 2013, 1, 3670; V. J. Chen, L. A. Smith, P. X. Ma, Biomaterials 2006, 27, 3973). According to Ma, et al., the highly roughened nanofibers contributed to improve proliferation of MC3T3-E1 murine osteoblasts and differentiation of the osteoblasts due to an increase in adsorption of cell adhesion proteins (fibronectin and vitronectin). Similarly, MG63 cells were favorably and preferentially adhered onto the roughened surface, and proliferated on the roughened surface since filopodia found adhesion sites having an influence on signal transmission associated with growth, proliferation and differentiation of the cells on the nanoscale roughened surface (see D. Yan, J. Jones, X. Y. Yuan, X. H. Xu, J. Sheng, J. C.-M. Lee, G. Q. Ma, Q. S. Yu, J. Biomed. Mater. Res. A 2013, 101, 963). Such research results proved that the proliferation and density of the cells on the PCL fibers having a nanoscale pattern were significantly high, compared to those of the cells on the untreated PCL fibers and the PCL fiber treated with plasma without any template. As a result, it was revealed that the nanoscale pattern formed on the surface of the fibers was able to improve initial cell attachment and proliferation.

From this Example, it could be seen that the SPET process according to one exemplary embodiment of the present invention was one of various simple plasma treatment methods which was able to be used to directly modify surfaces of the electrospun fibers, and was able to control the size of the patterned surface by controlling the size of holes of the template, thereby obtaining a nanoscale patterned surface capable of inducing significant cell attachment and proliferation.

EXAMPLE 2

The electrospun fiber mat obtained in Preparative Example 1 was subjected to oxygen plasma treatment.

Specifically, the plasma treatment was performed at a low frequency of 50 kHz, a power of 10 W, a pressure of $5.3 \times 10^{-1}$ Torr, and an oxygen flow rate of 10 sccm (standard cubic centimeters per minute).

First, a chamber was cleaned for 30 minutes to remove impurities by performing one plasma cycle on the chamber without any sample.

Then, electrospun fiber mats having a size of 20×20 mm$^2$ (151±18 μm thickness) were placed in the chamber, and subjected to plasma treatment for 10, 30, 60 and 120 minutes, respectively.

During SPET, a template (AAO, Anodisc filter, Whatman International Ltd., Maidstone, England) was placed on the electrospun fiber mat.

Also, an untreated PCL fibrous mat was used as the control.

In addition, a normally plasma-treated PCL fiber mat was obtained under the following plasma treatment conditions: 10 W, 10 sccm, an exposure time of 30 minutes, and without AAO template.

To modify a surface of the fabricated PCL fiber met, LF plasma (CUTE—MP/R, FEMTO, KOREA) (a low frequency of 50 kHz) having a generator frequency of 50 kHz was used, and the surface modification was performed in the presence of an 800 nm AAO template (ANODISC FILTER, Whatman International Ltd, Maidstone, England) to enhance surface modification efficiency.

Evaluation of Physical Properties (1) The surface morphology of the plasma-treated electrospun fibrous PCL mat was specified in the presence or absence of the template using a scanning electron microscope (SEM, SNE-3000M, SEC Co. Ltd., KOREA). Also, the morphology of the cells was evaluated using SEM at time points of 4 hours and 3 days after the cell culture.

(2) A surface roughness tester (Nanoview-m4151p, KOREA) was used to qualitatively measure surface roughness. A 3D profile of average roughness values was obtained using a phase-shifting interferometry (which was common optical technology for non-contact surface profilometry).

(3) The chemically bonding states and atomic concentrations in the specimen before and after plasma treatment were examined using X-ray photoelectron spectroscopy (XPS) (ESCA2000; Uckfield, UK, using a hemispherical electrostatic energy analyzer and Al Kα (1486.6 eV) X-ray light source). A base pressure in a specimen chamber was controlled to $10^{-9}$ Torr. The measured spectra were represented as a plot of the number of electrons versus electron binding energy at a fixed, small energy interval. The peak area and peak height sensitivity factor were used for quantification. All the surface compositions reported herein are represented by atomic % (atm %).

(4) To measure a water contact angle of a sample, one droplet (10 μl) of water was carefully dropped on a surface of a mat, and a contact angle was measured over time.

(5) The water absorption was calculated by measuring the weights of a sample before and after the sample was soaked in distilled water for 2 hours. An increase in percentage of water absorption was calculated according to the following Equation 2.

$$\text{Water absorption (\%)} = (W_{2h} - W_0)/W_0 \times 100 \quad \text{Equation 2}$$

In Equation 2, $W_{2h}$ represents the weight of a sample after 2 hours, and $W_o$ represents the original weight of the sample at a time point of zero.

(6) To measure mechanical properties, a specimen was cut into small strips (8×20 mm$^2$) A uniaxial test was performed using a tensile machine (Top-tech 2000, Chemilab, KOREA). A stress-strain curve for the scaffolds were recorded at an stretching speed of 0.5 mm/s All values are indicated by means±standard deviations (n=5).

In Vitro Cell Culture

A plasma-treated electrospun PCL mat (5×5 mm$^2$) was sterilized with 70% ethanol and ultraviolet (UV) light, and stationarily cultured overnight in a culture medium. MG63 cells (MG63 human source, ATCC CRL-1427, ATCC, Manassas, Va., USA) were used to evaluate the behavior of the cells cultured on the mat. The cells were cultured for up to four passages in a 24-well plate containing a Dulbecco's Eagle medium (DMEM; Thermo Scientific, Rogan, Utah, USA) supplemented with 10% fetal bovine serum (Hyclone) and 1% penicillin-streptomycin (Hyclone). The cells were collected by treatment with trypsin-ethylenediaminetetraacetic acid (EDTA), seeded on the mat at a density of 1×10$^5$ per sample, and cultured at 37° C. in an atmosphere of 5% $CO_2$. The medium was refreshed every other day.

After the cells were cultured for 4 hours, the mat was exposed to 0.15 mM Calcein AM and 2 mM ethidium homodimer-1 for 45 minutes in an incubator allowing observation of live and dead cells. A stained specimen was visualized under a microscope equipped with an epifluorescence part and an SPOT RT digital camera (SPOT imaging solution) (TE2000-S, Nikon, Japan). The stained image was captured. In this case, green and red represent live and dead cells, respectively. After 3 days of the cell culture, diamidino-2-phenylindole (DAPI) fluorescence staining was performed on the mat to detect the cell nuclei. Phalloidin (Invitrogen, Carlsbad, Calif., USA) staining was performed to visualize the actin cytoskeleton of the proliferated cells. Image-J software (National Institutes of Health, Bethesda, Md., USA) was used to measure the area of F-actin and the number of the cell nuclei after cell culture for 3 days.

ALP Activities

As a marker for osteoblast activities, ALP was used to measure and analyze release of p-nitrophenol (pNP) from p-nitrophenyl phosphate (pNPP).

The PCL mat on which the MG63 cells were seeded was mildly rinsed with phosphate buffered saline (PBS), and cultured for 10 minutes in a Tris buffer (10 mM, pH 7.5) containing a 0.1% Triton X-100 surfactant.

Next, 100 ml of a lysate was added to each well of the 96-well tissue culture plate containing 100 ml of a pNPP solution prepared using an ALP kit (procedure name: ALP-10; Sigma-Aldrich).

pNPP was converted into pNP and an inorganic phosphate in the presence of ALP. The ALP activity was measured from the absorbance at 405 nm using a microplate reader (Spectra III; SLT Lab Istruments, Salzburg, Austria).

The optical density (OD) for the ALP activity was normalized as a total protein content (OD value).

Alizarin Red S Staining

Calcium crystals were determined by Alizarin Red S staining of MG63 cells in a 24-well plate. The MG63 cells were cultured in DMEM supplemented with 50 mg/ml vitamin C and 10 mM β-glycerophosphate. The cells were washed three times with PBS, fixed in 70% (v/v) cold ethanol (4° C.) for an hour, and then dried in the air. The ethanol-fixed specimen was stained with 40 mM Alizarin Red S (pH 4.2) for an hour, and washed three times with purified water. The specimen was then de-stained with 10% cetylpyridinium chloride in a 10 mM sodium phosphate buffer (pH 7.0) for 15 minutes. An extent of staining was observed using an optical microscope, and the OD was measured at 562 nm using a Spectra III UV micro plate reader. The OD was normalized as a total protein content (OD value).

Total Protein Content

The total protein content was measured using BCA (bicinchoninic acid) protein analysis (Pierce Kit; Thermo Scientific, USA). A cell/scaffold specimen was cultured for 7 days and 14 days, and then analyzed. The specimen was washed with PBS, and lyzed in 1 mL of 0.1% Triton X-100. 200 mL of a BCA working reagent was added to an aliquot (25 ml) of the lysate, and the resulting mixture was then incubated at 37° C. for 30 minutes. The mixture was measured for absorbance at 562 nm using a plate reader.

Statistical Analysis

All the data are presented as a means±standard deviation. The statistical analysis was performed using SPSS software (product version 20.0; SPSS, Inc.), and included a single factor analysis of variation (ANOVA).

In all the analyses, * P<0.05 is considered to be of statistical significance. 'NS' represents a non-significant difference.

(1) Morphology of Plasma-Treated Electrospun Fiber

FIG. 6A provides SEM images of electrospun PCL microfibers treated with plasma for various exposure times (10, 30, 60, and 120 minutes) in the presence of an 800 nm AAO template. For the plasma treatment conditions, the plasma power was 10 W, and the oxygen flow rate was 10 sccm. As shown on the image, a significantly roughened surface was not developed at an exposure time of less than 120 minutes, but the fibers having nanoscaled roughness was obtained after exposure for 120 minutes.

FIG. 6B shows an SEM image of electrospun PCL microfibers treated under the same plasma processing conditions but treated with plasma in the absence of the template. As shown on the image, the surface of the PCL fibers was not roughened, and the slightly melted fibers were obtained. The SEM image of the AAO template (800 nm) is shown in FIG. 6C.

(2) Surface Roughness and XPS Results

According to some research results, the micro- and nanoscale patterns might have an influence on cell activities by inducing adsorption of proteins and monipulating cellular responces (including initial cell attachment, migration, growth, and even differentiation). In particular, the nanoscaled surface patterns were often observed to enhance bone matrix synthesis and osteointegration as well as initial osteoblast attachment, resulting from upregulation of genes such as actin and integrin. For these reason, the topography is an important parameter to determine a successful scaffold for tissue regeneration.

FIGS. 7A to 7C show the results of roughness for three PCL mats: the control, a PCL mat treated with plasma in the absence of a template, and a PCL mat treated with plasma in the presence of the template. The roughing of the fiber surfaces is shown in FIG. 7D. The average roughness, Ra, was obtained using a roughness curve. The Ra value represents roughness based on the thickness along the x-axis. The data on the average roughness (Ra) are shown in FIG. 7E, and obtained using the following Equation 3.

$$R_a = (\int |f(x)| dx)/L \quad \text{Equation 3}$$

In Equation 3, L represents a length of X-axis, and f(x) represents a roughness curve.

The plasma-treated fibers obtained using SPET has the highest average roughness (716±43 nm). On the other hand, the surface roughness value of the control and the fibers treated with plasma in the absence of the template were 27.3±3.5 nm and 126±13 nm, respectively, which corresponded to approximately 3% and approximately 18% of that of the plasma-treated fibers obtained using SPET. The average surface roughness of the plasma-treated fibers obtained using SPET was substantially similar to the size of the holes of the AAO template (800 nm).

The results showed that, although various AAO templates were not used to determine the control of surface roughness, SPET was able to be proposed to control the surface roughness. Some researchers recommended that the optimum average roughness to induce osteogenesis and/or osteointegration of osteoblasts was in a range of 700 to 900 nm According to Hatano, et al., the average roughness of 810 nm was optimal to induce the highest ALP activities in the MC3T3-E1 cells (see K. Hatano, H. Inoue, T. Kojo, T. Matusunaga, T. Tsujisawa, C. Uchiyama and Y. Uchida, Bone, 1999, 25, 439).

In the previous research, although the optimum surface roughness varied according to various parameters such as the cell-type, substitute stiffness, etc., the cell-imprinted surface having a roughness of 702±87 nm showed excellent ALP activities and calcium deposition(MG63) in the osteoblasts.

For this reason, the roughened surface (Ra=716±43 nm) obtained in the presence of the template (hole size: 800 nm) using SPET was considered to significantly induce high cell proliferation and differentiation.

FIGS. 8A to 8C show the XPS spectra of the fibrous PCT mats treated with plasma in the presence and absence of the template, and the untreated mat, respectively. These spectra are summarized in Table 2 (chemical composition and relative area corresponding to different chemical bonds).

TABLE 2

|  | Chemical compositions (%) | | Relative area (%) corresponding to other chemical bonds | | | | |
|---|---|---|---|---|---|---|---|
|  |  |  | Carbon | | Oxygen | | |
|  | Carbon | Oxygen | C—H | C—O—O | —COOH | C—O—C | —OH |
| Control | 90.95 | 9.05 | 86.04 | 4.91 | 6.11 | 1.51 | 1.43 |
| PCL mat treated w/o template | 89.62 | 10.38 | 84.52 | 5.1 | 5.15 | 2.79 | 2.44 |
| PCL mat treated with template | 84.93 | 15.08 | 78.79 | 6.14 | 10.67 | 2.47 | 1.94 |

As seen from the results listed in Table 2, it was revealed that the chemical compositions of the surface of the untreated PCL fiber mat included 9.05% oxygen and 90.95% carbon. The surface compositions upon plasma treatment in the absence of the template included 10.38% oxygen and 89.62% carbon. The PCL mat treated with plasma in the presence of the template had surface compositions of approximately 15.1% oxygen and approximately 84.9% carbon.

A difference between a normally plasma-treated surface and surfaces treated using SPET was due from the use of different plasma exposure times (30 minutes in the case of the PCL mat treated in the absence of the template; and 2 hours in the case of the PCL mat treated in the presence of the template).

Based on these results, it was assumed that an increase in content of oxygen on the surface after the plasma treatment was caused by chemical bonding, thereby improving hydrophilicity of the plasma-treated PCL mat.

(3) Water Contact Angle and Water Absorption

Hydrophilicity was known to have a significant influence on various cellular responces (attachment cell attachment, migration, proliferation, and even physiological activities). In this research, the hydrophilicity was evaluated by measuring a water contact angle (WCA).

As shown in FIGS. 9A to 9C, the WCA of the untreated PCL mat, the normally plasma-treated PCL mat, and the PCL mat treated using SPET were 102±2°, 13±1°, and 23±3° at a time point of 5 minutes, respectively. The plasma treatment significantly increased hydrophilicity of the fiber PCL mat. The WCA of the PCL mat treated using SPET was generally slightly higher than that of the plasma-treated PCL mat.

Such a phenomenon resulted from the physically roughened surface, which was obtained using selective treatment through the 800 nm template. In this case, water was slightly repelled into patterns such as a lotus leaf fashion.

The WCA was not substantially identical to that of the normally treated PCL mat, and the modification of the PCL mat using SPET was sufficient to have an influence on cell activities including initial attachment and growth of cells.

Generally, the water absorption have an influence on homogenous distribution and structural morphology of grown tissues. The water absorption was measured by weighing the PCL mat after the PCL mat was soaked into distilled water for 2 hours, and before the PCL mat was soaked into distilled water.

FIG. 9D presents the results of water absorption of three samples. The water absorption of the plasma-treated PCL mat was significantly higher than that of the untreated PCL mat.

Also, the PCL mat treated using SPET has slightly lower water absorption than the normally treated PCL mat. A difference in water absorption properties resulted from the same phenomenon as described above as the WCA results. Such results presented that the plasma-treated PCL mat was able to sufficiently retain body fluids and nutrients in vitro and in vivo in various cell culture systems.

(4) Tensile Properties

To observe a change in mechanical properties before and after the plasma treatment, the stress-strain curves for three types of PCL mats were measured. FIG. 10A includes stress-strain curves for the PCL mats. A tensile results were obtained using a tensile mode. For the three types of the PCL mats, the stress-strain curves included two characteristic regions, which were a tensile area and a cohesive strain-relaxation area.

FIG. 10B shows that the plasma-treated PCL mat in the presence of the template has the highest roughness. Nevertheless, the Young's modulus and the maximum stress of the plasma-treated PCL were not significantly different.

Such results indicated that the SPET method did not have a significant influence on the tensile properties of the PCL microfibers. The detailed properties of the tensile test are as listed in the following Table 3. Similar results were reported previously.

TABLE 3

|  | Control | PCL treated w/o template | PCL treated with template |
|---|---|---|---|
| Young's modulus (MPa) | 8.9 ± 0.8 | 8.9 ± 1.2 | 8.4 ± 0.4 |
| Maximum stress (MPa) | 6.6 ± 0.1 | 6.8 ± 0.4 | 5.4 ± 1.3 |
| Strain at break (%) | 564 ± 157 | 573 ± 120 | 558 ± 165 |

(5) In Vitro •Cell Culture Results

FIGS. 11A to 11C provide fluorescent images of the control, the PCL fibrous mat treated with plasma in the absence of the template, and the PCL mat treated with plasma using an SPET method, on which the cells were all cultured for 4 hours.

Attached cells were stained with calcein AM and ethidium homodimer-1 to indicate the live and dead cells in green and red, respectively.

As seen from the images, a larger amount of the seed cells were attached to, and proliferated on the PCL microfibers treated using an SPET method at the beginning, compared to the other mats (the control (an untreated PCL mat) and the PCL fibrous mat treated with plasma in the absence of the template). As shown as the enlarged image, the cells were also highly stretched on the PCL mat treated using SPET. Such results presented that strong stimulation of osteogenesis was able to be achieved using the PCL microfibrous mat having a nanoscale surface patterns.

For the control, the normally treated PCL mat, and the PCL fibrous mat treated using SPET, the nuclei of osteoblast-like cells (MG63) and actin were cultured for 3 days, and examined using DAPI (blue) and phalloidin(red) fluorescent images.

As seen from the live-dead staining, F-actin was more homogenously distributed on the PCT mat fabricated using SPET, compared to the control and the normally treated PCL mat (FIGS. 12A to 12C). The number of the nuclei and the area of F-actin measured using Image-J software were significantly higher in the case of the PCL mat treated using SPET, compared to the other PCL mats (FIGS. 12D to 12E). Such a phenomenon resulted from the physically patterned surface of the PCL mat capable of promoting initial cell attachment and proliferation.

When the osteoblast-like cells were cultured for 4 hours and 3 days, the morphology of the osteoblast-like cells were observed using SEM. Typical the SEM images are shown in FIGS. 13A to 13C. Generally, a certain shape was able to be used to control the morphology of the osteoblasts within nano-scaled surface properties.

In particular, the cells formed in the form of island nano-structuralized on the plasma-treated surface were reported to have well-defined filopodia and/or lamellipodia.

As seen from the SEM images, the filopodia and lamellipodia were observed more clearly on the nano-structuralized surface of the plasma-treated PCL mat, compared to the control and the normally plasma-treated PCL mat (red dotted circles in the SEM image).

(6) ALP Activity and Calcium Mineralization

The ALP activities (Table 4) normalized as the total protein content of the MG63 osteoblast-like cells on the control, and the PCL mats treated with plasma in the presence and absence of the template were measured using pNPP at time points of 7 days and 14 days (FIG. 14A). The value of the control was set to 100%. All the experimental groups showed ALP activities increasing from 7 days to 14 days. However, the PCL fibrous mat treated using SPET showed significantly increased ALP activities at each time point of measurement, compared to the control and the mat treated in the absence of the AAO template.

TABLE 4

| Optical density (OD) | Control | PCL mat treated w/o template | PCL mat treated with template |
|---|---|---|---|
| 7 days | 0.244 ± 0.01 | 0.258 ± 0.08 | 0.253 ± 0.01 |
| 14 days | 0.255 ± 0.02 | 0.309 ± 0.01 | 0.315 ± 0.02 |

The calcium depositions normalized as the total protein content (Table 4) at time points of 7 days and 14 days for the osteoblast-like cells on the control and the fibrous mat treated in the presence and absence of the template are shown in FIG. 15B. The calcium deposition was greater in the case of the plasma-treated PCL mats, compared to the control. Such results were similar to those reported by Habinovic, et al. (see A. Nandakumar, Z. T. Birgani, D. Santos, A. Mentink, N. Auffermann, K. van derWerf, M. Bennink, L. Moroni, C. van Blitterswijk and P. Habibovic, Biofabrication, 2013, 5, 015006j). In the studies conducted by Habinovic, et al., the oxygen plasma-treated PCL mat showed positive osteogenic differentiation including ALP activities and osteonectin expression in hMSCS. They concluded that the improvement observed for the plasma-treated fiber mats was due from the nanoscale surface pattern capable of serving as signals for cell fate regulation in fibrous meshes.

Also, the calcium deposition was accelerated in the PCL mat treated using SPET, compared to the normally plasma-treated PCL mat.

This phenomenon resulted from the homogenously patterned nanoscale surface of the PCL mat treated using SPET, and thus come from a result of micro-environmental conditions more favorable to cell attachment and proliferation, compared to the normally plasma-treated PCL mat.

To qualitatively analyze an effect of the calcium deposition, optical images after an Alizarin Red S staining method were obtained. The optical images are shown in FIGS. 15A to 15C.

It was revealed that the cells on the PCL mat treated using SPET showed higher mineralized matrix deposition, compared to the control and the normally plasma-treated PET mat.

A method of forming a nanoscale surface pattern on electrospun PCL fibers was specifically described in Examples, and such a physical pattern was achieved using selective plasma treatment in the presence of the AAO template. The nanoscale patterned surface was evaluated using X-ray photoelectron spectroscopy (XPS) and phase analysis. As a result, the roughness Ra of the pattern formed on the surface of the electrospun PCL fibers was 716±43 nm, which was generally different from the fact that the normally plasma-treated surface showed relatively low roughness (Ra=126±13 nm). To evaluate the probability of using the microfibrous PCL mat having a nanoscale roughened surface as a biomedical scaffold, osteoblasts (MG63) were cultured. Also, the ALP activities were determined using fluorescence analysis (live/dead analysis and 4,6-diamidino-2-phenylindole(DAPI)/phalloidin analysis), and the calcium deposition was analyzed. The plasma-treated PCL mat selectively showed excellent biological activities such as cell proliferation and differentiation, compared to the untreated PCL fiber mat (the control) and the normally plasma-treated fiber mat.

According to Examples as described above, various simple plasma treatment methods supplemented with the AAO template were useful in generating a scaffold of electrospun PCL fibers having a highly roughened surface. Such methods were useful in obtaining a nanoscale pattern widely controllable under various plasma treatment conditions. The PCL fibrous mat treated using SPET showed highly improved biological activities, compared to the untreated fibers and the normally plasma-treated PCL fibers. Particularly, the treated PCL mats showed superior initial cell attachment and proliferation, ALP activities, and calcium deposition, compared to the other PCL mats. Based on these results, it was concluded that the resulting PCL fibrous mats had high probability as biomaterials for various applications to tissue regeneration.

The present invention can be useful in fabricating a polymeric nanofiber showing modified structural properties and hydrophilic properties, which is structuralized without applying higher power than normal plasma treatment methods, since the polymeric nanofiber is subjected to plasma treatment to solve the problems regarding a process for surface modification. Also, the present invention can be useful in modifying a surface of a polymer, which is very sensitive to the temperature, and has problems in that a surface structure of the polymer itself is easily damaged and deformed when the entire surface of the polymer was surface-modified, into a surface having hydrophilic properties without causing damage to the surface of fibers. In addition, the present invention has an advantage in that it is possible to effectively surface-modify synthetic and natural polymers used as biomaterials. Additionally, the present invention can be useful in preventing modification and deformation of the biomaterials to be engrafted into the human body since surface modification efficiency is maximized due to the use of the AAO template, and plasma is used at a low frequency band to reduce generation of heat, and also useful in maximizing a modification effect for the use of plasma at a low frequency band. Further, the present invention has an advantage in that it is possible to control the size of the AAO template to be surface-modified since the area to which plasma is transferred may be controlled by controlling the size of the holes in the AAO template. Ultimately, when a patient is engrafted with a scaffold whose surface is modified using such a process, an apparent environment in which target cells may grow well to an engrafted site, thereby realizing a rapid regenerative ability and shortening of a treatment period.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of modifying a surface of a polymeric nanofiber, comprising:
    performing low-frequency plasma treatment on the polymeric nanofiber to modify the surface of the polymeric nanofiber,
    wherein the low-frequency plasma treatment is low-frequency oxygen plasma treatment and performed in a state in which an anodic aluminum oxide template covers the polymeric nanofiber, and
    wherein the low-frequency plasma treatment is performed until the modified surface has a surface roughness, Ra, in a range of 650 to 800 nm.

2. The method of claim 1, wherein the polymeric nanofiber is a polymeric nanofiber mat.

3. The method of claim 1, wherein the polymeric nanofiber comprises at least one selected from the group consisting of polycaprolactone (PCL), poly(lactic acid) (PLA), poly(glycolic acid) (PGA), poly(lactic acid-co-glycolic acid) (PLGA), and a mixture thereof.

4. The method of claim 3, wherein the polymeric nanofiber comprises polycaprolactone (PCL).

5. The method of claim 1, wherein the plasma treatment is performed for 120 minutes to 240 minutes under conditions of a frequency of 50 kHz, a power of 10 to 30 W, an oxygen flow rate of 10 to 15 sccm, and a pressure of $5.1 \times 10^{-1}$ to $5.4 \times 10^{-1}$ Torr.

6. The method of claim 1, wherein the anodic aluminum oxide template has a plurality of holes having an average diameter of 100 to 800 nm formed therein.

7. The method of claim 1, wherein the low-frequency plasma treatment is performed until the modified surface comprises a plurality of nanoscale patterns containing hydrophilic groups chemically bound to the polymeric nanofibers.

\* \* \* \* \*